(12) United States Patent
Chinta et al.

(10) Patent No.: US 10,179,323 B2
(45) Date of Patent: Jan. 15, 2019

(54) METAL OXIDE CATALYST SYSTEMS FOR CONVERSION OF ETHANOL TO BUTADIENE

(71) Applicant: FINA TECHNOLOGY, INC., Houston, TX (US)

(72) Inventors: Sivadinarayana Chinta, Sugar Land, TX (US); Kaushik Gandhi, League City, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 0 days.

(21) Appl. No.: 15/175,727

(22) Filed: Jun. 7, 2016

(65) Prior Publication Data

US 2017/0349503 A1 Dec. 7, 2017

(51) Int. Cl.
| | |
|---|---|
| C07C 1/24 | (2006.01) |
| C07C 1/20 | (2006.01) |
| B01J 23/06 | (2006.01) |
| B01J 23/36 | (2006.01) |
| B01J 23/20 | (2006.01) |
| C07C 45/00 | (2006.01) |
| C07C 1/207 | (2006.01) |
| B01J 23/80 | (2006.01) |
| B01J 29/16 | (2006.01) |
| B01J 38/10 | (2006.01) |
| B01J 23/92 | (2006.01) |
| B01J 37/00 | (2006.01) |

(52) U.S. Cl.
CPC .............. *B01J 23/06* (2013.01); *B01J 23/20* (2013.01); *B01J 23/36* (2013.01); *B01J 23/80* (2013.01); *B01J 29/163* (2013.01); *C07C 1/20* (2013.01); *C07C 1/2076* (2013.01); *C07C 45/002* (2013.01); *B01J 23/92* (2013.01); *B01J 37/0018* (2013.01); *B01J 38/10* (2013.01); *B01J 2229/186* (2013.01); *B01J 2229/42* (2013.01); *B01J 2523/00* (2013.01); *C07C 2521/06* (2013.01); *C07C 2521/08* (2013.01); *C07C 2521/10* (2013.01); *C07C 2523/06* (2013.01); *C07C 2523/20* (2013.01); *C07C 2523/36* (2013.01); *C07C 2523/72* (2013.01); *C07C 2523/80* (2013.01); *C07C 2529/16* (2013.01)

(58) Field of Classification Search
CPC .................................... C07C 1/24; C07C 1/20
USPC .......................................... 585/603, 606, 609
See application file for complete search history.

(56) References Cited

U.S. PATENT DOCUMENTS 2,438,464 A * 3/1948 Spence .................... B01J 21/08
502/240

OTHER PUBLICATIONS

"Investigations into the conversion of ethanol into 1,3-butadiene" Jones et al; 2011, pp. 267-272.*

* cited by examiner

*Primary Examiner* — Thuan D Dang
(74) *Attorney, Agent, or Firm* — Albert Shung

(57) ABSTRACT

A process includes reacting a feed stream containing ethanol and optionally acetaldehyde in a dehydration reactor in the presence of a dehydration catalyst system having a Group 4 or Group 5 metal oxide and a support. The process includes obtaining a product stream containing butadiene from the dehydration reactor. Another process includes reacting a feed stream containing ethanol and optionally acetaldehyde in a dehydration reactor in the presence of a dehydration catalyst system containing a tungsten oxide supported on a zeolite or a tantalum oxide supported on a zeolite. The process includes obtaining a product stream containing butadiene from the dehydration reactor.

16 Claims, 8 Drawing Sheets

METAL OXIDE CATALYST SYSTEMS FOR CONVERSION OF ETHANOL TO BUTADIENE

CROSS-REFERENCE TO RELATED APPLICATIONS

Not applicable.

FIELD

Embodiments of the present disclosure generally relate to conversion of ethanol to butadiene. More particularly, embodiments of the present disclosure relate to the use of supported metal oxide catalyst systems for conversion of ethanol to butadiene.

BACKGROUND

Traditionally, 1,3-butadiene is manufactured primarily as a co-product of steam cracking to produce ethylene in the United States, Western Europe, and Japan. In certain parts of the world where biomass for fermentation is plentiful, 1,3-butadiene is produced from ethanol. Butadiene has also been produced by the dehydrogenation of n-butane and oxydehydrogenation of n-butenes.

Bioethanol is a renewable alternative to fossil-derived gasoline. For the purposes of this disclosure, bioethanol is defined as ethanol manufactured from plant materials. Various feedstocks may be used in the production of bioethanol, including sugars, starches and cellulosic biomass (e.g., straw, wood, etc.). Bioethanol may be converted to butadiene.

SUMMARY

The present disclosure provides for a process that includes reacting a feed stream containing ethanol in a dehydration reactor in the presence of a dehydration catalyst system containing a Group 4 or Group 5 metal oxide and a support. The process includes obtaining a product stream containing butadiene from the dehydration reactor.

The disclosure provides for another process that includes reacting a feed stream containing ethanol and optionally acetaldehyde in a dehydration reactor in the presence of a dehydration catalyst system containing a tungsten oxide supported on a zeolite or a tantalum oxide supported on a zeolite. The process includes obtaining a product stream containing butadiene from the dehydration reactor.

BRIEF DESCRIPTION OF DRAWINGS

The present disclosure may be understood from the following detailed description when read with the accompanying figures.

DETAILED DESCRIPTION

Figure 1A:
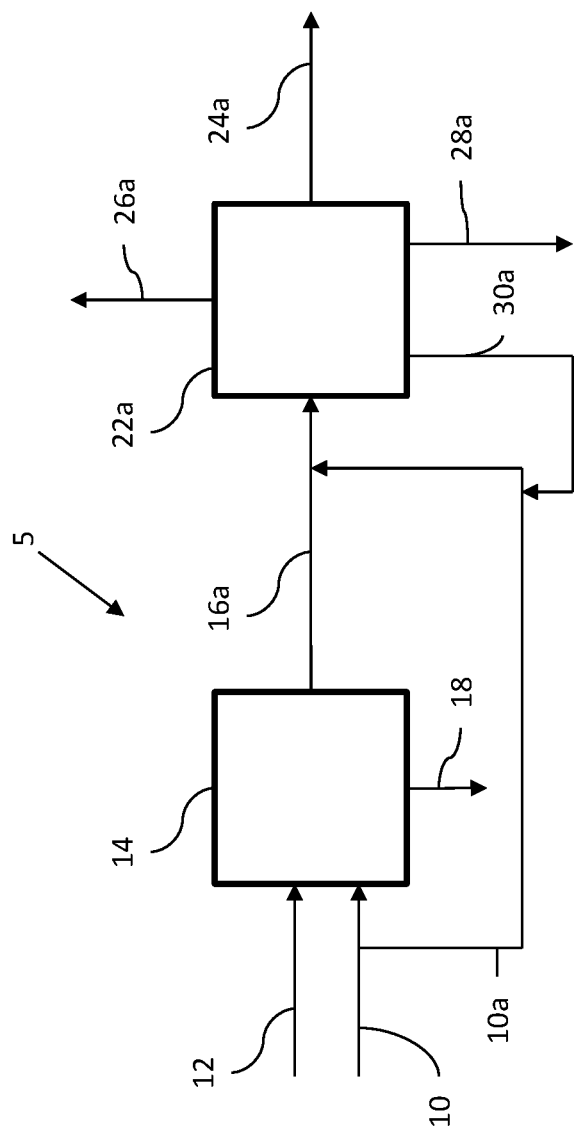
FIG. 1A depicts a reaction flow diagram in accordance with certain embodiments of the present disclosure.

A detailed description will now be provided. The following disclosure includes specific embodiments, versions and examples, but the disclosure is not limited to these embodiments, versions or examples, which are included to enable a person having ordinary skill in the art to make and use the disclosure when the information in this application is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Certain embodiments of the present disclosure relate to a process for producing butadiene from ethanol. Conversion of ethanol, such as bioethanol, to butadiene may be performed by a one-step process (i.e., the Lebedev process) or a two-step process (i.e., the Ostromislensky process). The two-step Ostromislensky process proceeds generally according to the following reaction schemes Ia and Ib:

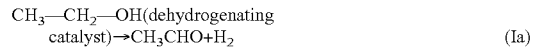

(Ia)

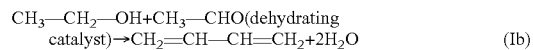

(Ib)

Reaction scheme Ia exhibits a heat of reaction $\Delta H=+16.51$ kcal/mole, and reaction scheme Ib exhibits a heat of reaction $\Delta H=+7.11$ kcal/mole. As shown by reaction scheme $Ia_2$ below, the dehydrogenation step (Ia) may be carried out autothermally in the presence of air or oxygen (e.g., the Veba-Chemie process), with the concomitant combustion of the hydrogen formed supplying the necessary heat of dehydrogenation.

($Ia_2$)

Reaction scheme $Ia_2$ exhibits a heat of reaction $\Delta H=-43$ kcal/mole (catalytic).

The one-step Lebedev process generally proceeds according to the following reaction scheme II:

(II)

Reaction scheme II exhibits a heat of reaction $\Delta H=+23.63$ kcal/mole. The combination of the two-step Ostromislensky process using the autothermal dehydrogenation route ($Ia_2$) may have a lower net heat of reaction than the one-step Lebedev process. Without being bound by theory, it is believed that butadiene produced by the one-step Lebedev process is typically less than 80% pure as compared with a typical 98% or better purity of butadiene produced by the two-step Ostromislensky process. The two-step Ostromislensky process may exhibit a lower deactivation rate of catalyst. The first step of the two-step Ostromislensky process (Ia or Ia$_2$) may exhibit a 30-50% conversion of ethanol to acetaldehyde at 90-95% selectivity.

Figure 1B:
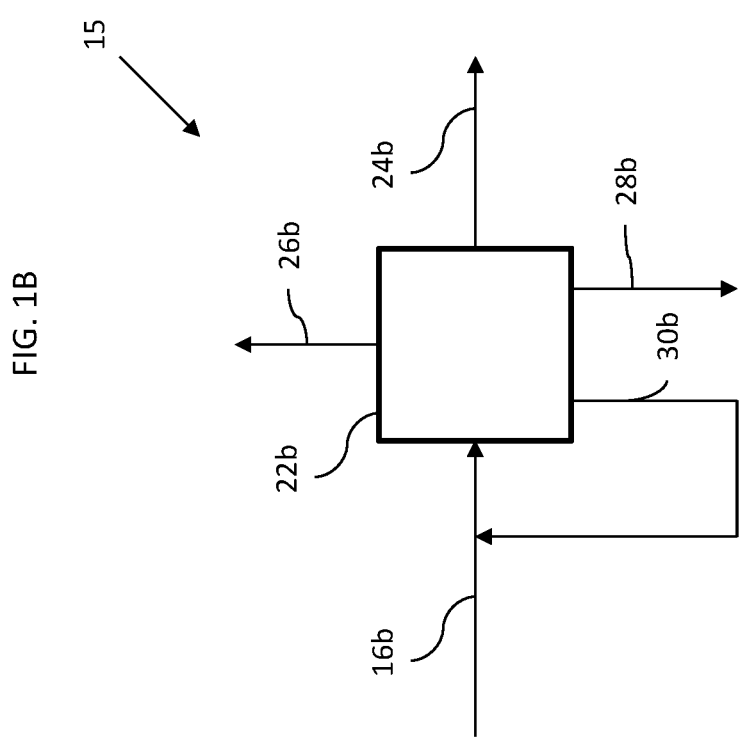
FIG. 1B depicts a reaction flow diagram in accordance with certain embodiments of the present disclosure.

FIG. 1A is a flow diagram of two-step conversion process 5 for conversion of ethanol to butadiene using the two-step Ostromislensky process, and FIG. 1B is a flow diagram of one-step conversion process 15 for conversion of ethanol to butadiene using the one-step Lebedev process.

With reference to two-step conversion process 5 in FIG. 1A, ethanol feed stream 10 may be fed to dehydrogenation reactor 14. In certain embodiments, such as that depicted in FIG. 1A, oxygen may be fed to dehydrogenation reactor 14 through oxygen feed stream 12. Oxygen feed stream 12 may include air. Although shown as separate streams, ethanol feed stream 10 and oxygen feed stream 12 may be combined prior to dehydrogenation reactor 14. Ethanol feed stream 10 may contain ethanol, including, but not limited to, bioethanol. Dehydrogenation reactor 14 may contain any dehydrogenation catalyst system known to one skilled in the art. In certain embodiments, the dehydrogenation catalyst may contain silver. Within dehydrogenation reactor 14, at least some ethanol from ethanol feed stream 10 may react in the presence of the dehydrogenation catalyst system and, in certain embodiments, oxygen, to form acetaldehyde. The temperature in dehydrogenation reactor may range, in certain embodiments, from 260 to 310° C. Products from dehydrogenation reactor 14 are discharged through dehydrogenation product stream 16a. Dehydrogenation reactor product stream 16a may contain acetaldehyde and unreacted ethanol. Reaction of ethanol feed stream 10 in dehydrogenation reactor 14 may also form first side product stream 18 containing water.

Dehydrogenation reactor 14 may be located upstream of dehydration reactor 22a. In certain embodiments, dehydration reactor 22a may be a fixed bed continuous flow reactor, for example. Dehydrogenation reactor product stream 16a may be fed to dehydration reactor 22a. In some embodiments, dehydrogenation bypass stream 10a, which is a portion of ethanol feed stream 10, may be fed to dehydration reactor 22a. For example and without limitation, a portion of stream ethanol feed stream 10 may be diverted as dehydration bypass stream 10a and combined with dehydrogenation reactor product stream 16a upstream of dehydration reactor 22a or fed to dehydration reactor 22a separately from dehydrogenation reactor product stream 16a.

Within dehydration reactor 22a, ethanol and acetaldehyde from dehydrogenation reactor product stream 16a may react in the presence of a dehydration catalyst system including a Group 4 metal oxide, Group 5 metal oxide, or tungsten oxide and a support to form dehydration product stream 24a. Dehydration product stream 24a may contain 1,3-butadiene. Dehydration product stream 24a may be obtained from dehydration reactor 22a. In some embodiments, dehydration product stream 24a is in the gas phase.

In some embodiments, two-step conversion process 5 includes recycling dehydration recycle stream 30a from dehydration reactor 22a. Dehydration recycle stream 30a may contain unreacted ethanol from dehydration reactor 22a. Dehydration recycle stream 30a may contain ethanol, acetaldehyde, butadiene, diethyl ether, other oxygenates, or combinations thereof. Two-step conversion process 5 may include feeding dehydration recycle stream 30a into dehydration reactor 22a. For example and without limitation, dehydration recycle stream 30a may be combined with dehydrogenation bypass stream 10a, dehydrogenation reactor product stream 16a, or both. In some embodiments, dehydration recycle stream 30a may be fed to dehydration reactor 22a separately from dehydrogenation bypass stream 10a and dehydrogenation reactor product stream 16a. In some embodiments, a reflux ratio ranges from 0.5 to 1.0. "Reflux ratio" as used herein refers to the ratio of the amount of dehydration recycle stream 30a to the amount of dehydrogenation reactor product stream 16a and optionally dehydrogenation bypass stream 10a fed to dehydration reactor 22a, as determined by volume.

Reacting dehydrogenation reactor product stream 16a in dehydration reactor 22a in the presence of the dehydration catalyst system may form second side product stream 26a containing $H_2$ and a third side product stream 28a containing water. In some embodiments, third side product stream 28a is in the liquid phase. While second side product steam 26a and dehydration product stream 24a are shown as exiting dehydration reactor 22a separately, the contents of second side product steam 26a and dehydration product stream 24a may exit dehydration reactor 22a as a single gaseous effluent stream and may be separated downstream of dehydration reactor 22a.

With reference to FIG. 1B, reaction in dehydration reactor 22b may occur in substantially the same manner as in dehydration reactor 22a as discussed herein, with the following differences. Reaction in dehydration reactor 22b differs from reaction in dehydration reactor 22a in that dehydration reactor feed stream 16b is not an effluent from an upstream dehydrogenation reactor, and contains ethanol and, in at least some embodiments, does not contain acetaldehyde. As in dehydration reactor 22a, reaction in dehydration reactor 22b may produce dehydration product stream 24b containing 1,3-butadiene; second side product stream 26b containing $H_2$; and third side product stream 28b containing water. Also as in dehydration reactor 22a, dehydration recycle stream 30b from dehydration reactor 22b may be obtained. Dehydration recycle stream 30b may have the same constituents as dehydration recycle stream 30a, and may be recycled to dehydration reactor 22b in the same manner as dehydration recycle stream 30a is recycled to dehydration reactor 22a.

Effluent from dehydration reactor 22a or dehydration reactor 22b may include liquid effluents, such as ethanol, acetaldehyde, butadiene, diethyl ether, ethylene, ethoxy ethane, ethoxy butane, diethoxy ethane, ethoxy butane, 2-butenal, other oxygenates, or combinations thereof, which may be present in third side product stream 28a or 28b, for example. Effluent from dehydration reactor 22a or dehydration reactor 22b may include gaseous components, such as butadiene, CO, $CO_2$, $H_2$, methane, and other $C_4$ and lighter components, which may be present in second side product stream 26a or 26b or in dehydration product stream 24a or 24b. In some embodiments, effluent from dehydration reactor 22a or dehydration reactor 22b may also include gaseous components, such as $N_2$, $O_2$, CO, $CO_2$, $CH_4$, $C_2H_4$, $C_2H_6$, $C_2H_2$, $C_{6+}$, $C_3H_6$, $C_3H_8$, $C_4H_6$, $C_4H_8$, $C_4H_{10}$, $C_5H_{10}$, $C_5H_{12}$, or combinations thereof, which may be present in second side product stream 26a or 26b or in dehydration product stream 24a or 24b.

Figure 2:
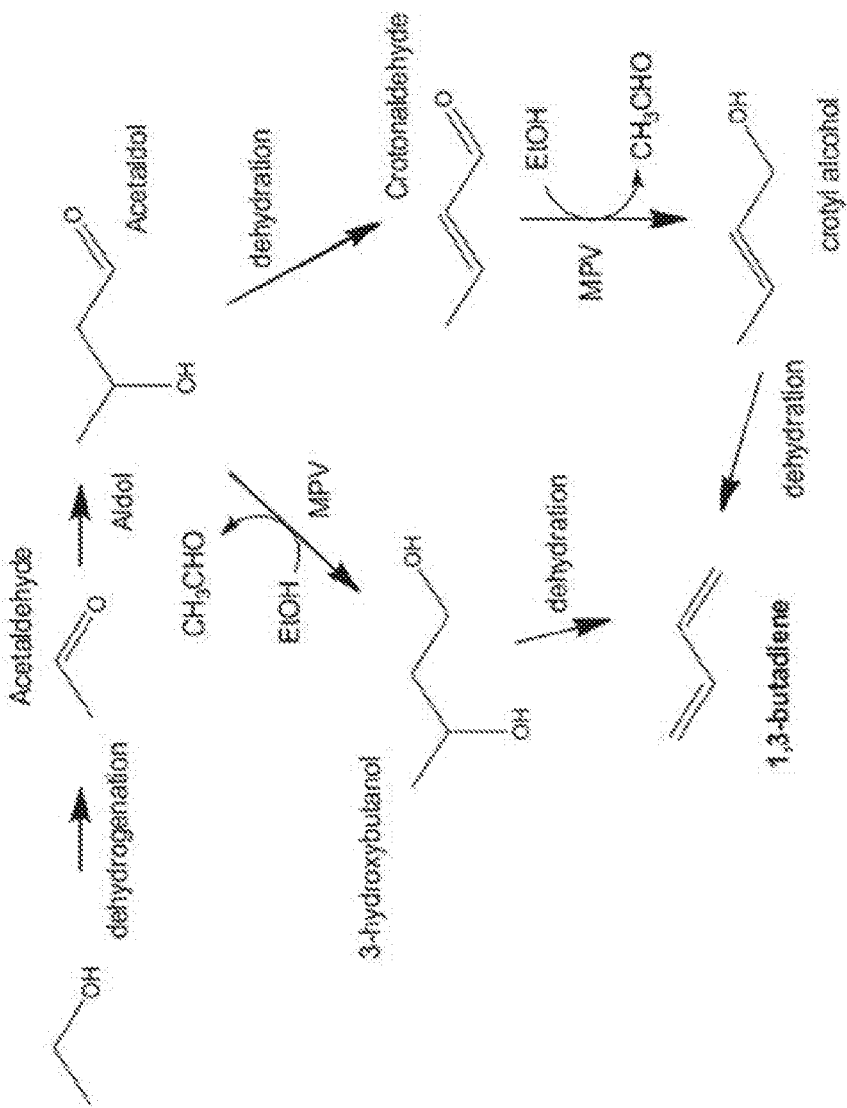
FIG. 2 depicts a reaction mechanism for the formation of butadiene from ethanol in accordance with certain embodiments of the present disclosure.

Without being bound by theory, conversion of ethanol to butadiene may generally proceed according to the reaction mechanism shown in FIG. 2, by aldol condensation between two acetaldehyde molecules formed upon ethanol dehydrogenation. It is believed that the aldol-addition product, 3-hydroxybutanal, may yield crotonaldehyde by dehydration, which may then further be hydrogenated and dehydrated to yield butadiene. As shown in FIG. 2, the reaction mechanism generally involves the following principal steps: (1) formation of acetaldehyde from ethanol by dehydrogenation; (2) acetaldehyde aldol condensation (acetaldol or 3-hydroxybutanal); (3) followed by formation of crotonaldehyde; (4) reaction of crotonaldehyde with ethanol on the surface of a metal oxide dehydration catalyst system; (5) hydrogen transfer via a Meerwein-Ponndorff type mechanism; and (6) dehydration to butadiene. Thus, ethanol acts as a source of acetaldehyde, and subsequently as a source of hydride.

Figure 3:
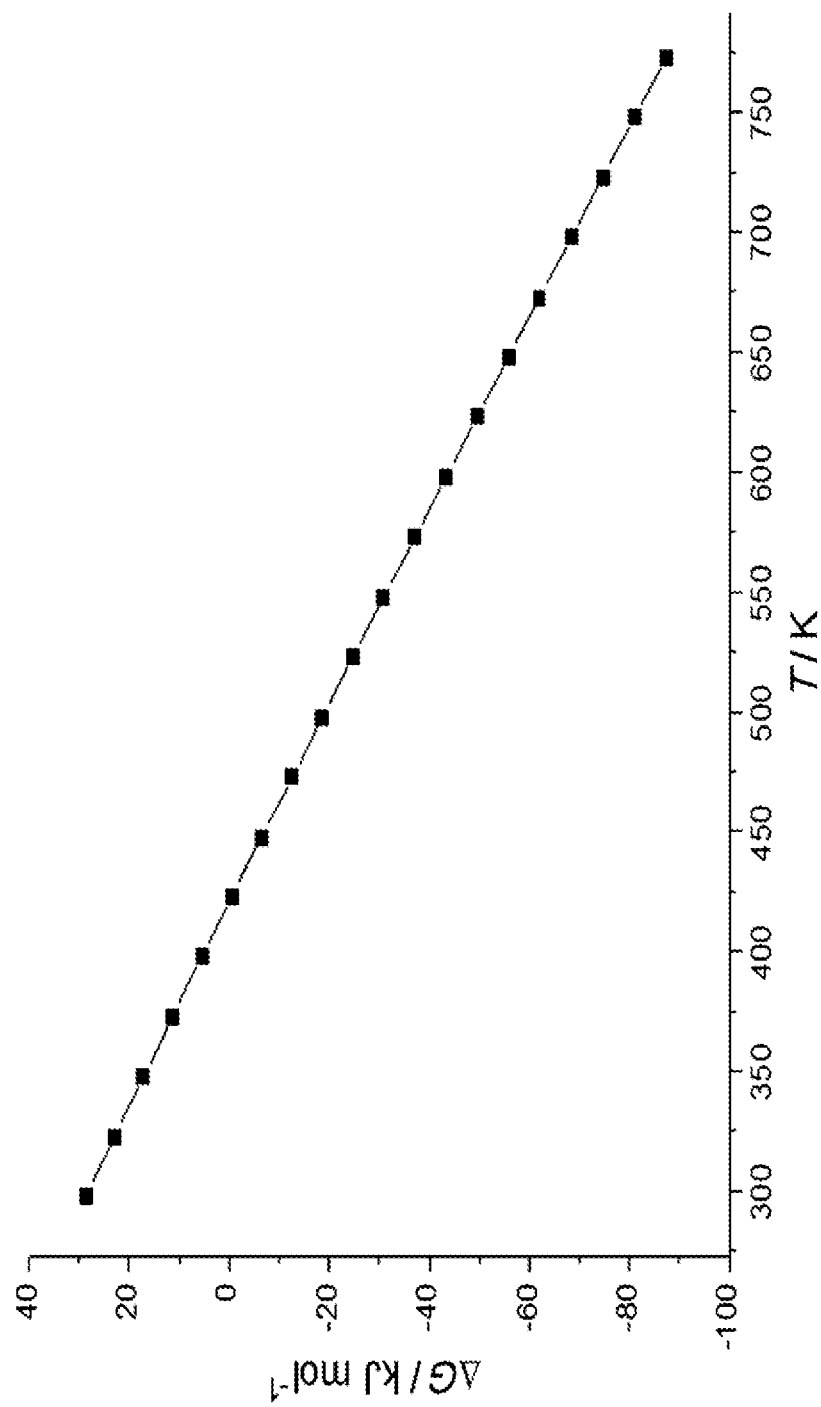
FIG. 3 is a line graph depicting free energy change for the formation of butadiene from ethanol as calculated by the HSC7 software package in accordance with certain embodiments of the present disclosure.

The feasibility of butadiene production from ethanol, as well as a favorable operational window for this reaction, has been assessed by thermodynamic equilibrium calculations using the HSC7 software package, as shown in FIG. 3. With reference to FIG. 3, butadiene production from ethanol may be performed at temperatures of at least 148° C. (423 K) and at most 425° C. (698 K), for example.

Calculated Gibbs free energies at different temperatures are summarized in Table 1 for the steps proposed for the aldehyde condensation route. As can be seen from Table 1, the second step, that is, the coupling of two acetaldehyde molecules to 3-hydroxybutanal, is unfavorable, but may be compensated for by the subsequent condensation reaction yielding crotonaldehyde, which is highly exergonic. In the acetaldehyde condensation route, crotonaldehyde may either be reduced by ethanol or by hydrogen that is generated in the first step.

Pressure in dehydration reactor 22a or dehydration reactor 22b may be any pressure set forth in any of the Tables provided herein or utilized in any of the examples disclosed herein.

Liquid hourly space velocity (LHSV) in dehydration reactor 22a or dehydration reactor 22b during reaction of dehydrogenation reactor product stream 16a or dehydration reactor feed stream 16b may range from 0.1 to 0.8 $hr^{-1}$, 0.2 to 0.6 $hr^{-1}$, 0.31 to 0.49 $hr^{-1}$, 2 to 4 $hr^{-1}$, or 1 to 5 $hr^{-1}$. LHSV in dehydration reactor 22a or dehydration reactor 22b may be any LHSV as set forth in any of the Tables provided herein or utilized in any of the examples disclosed herein.

A volumetric ratio of ethanol to acetaldehyde in dehydrogenation reactor product stream 16a or dehydration reactor feed stream 16b may be from 9:1 to 1:0, 5:1 to 1:1, 0.9:0.1 to 0.7:0.3, 0.8:0.2 to 0.2:0.8, or 4:1, or 1:1, or 2.5:1. The volumetric ratio of ethanol to acetaldehyde in dehydration reactor 22a or dehydration reactor 22b may be any volumetric ratio as set forth in any of the Tables provided herein or utilized in any of the examples disclosed herein. In embodiments, ethanol is present in excess with respect to the amount of acetaldehyde, as determined by volume percent. Without being bound by theory, it is believed that the presence of excess ethanol provides larger yields of butadiene, which allows the reaction of crotonaldehyde with ethanol to proceed. In some embodiments, the feed stream to the dehydration reactor 22a or 22b does not contain acetaldehyde, such that acetaldehyde is not present in dehydrogenation reactor product stream 16a or dehydration reactor feed stream 16b.

TABLE 1

| Step | Reaction | ΔG [kJ $mol^{-1}$] | | |
|---|---|---|---|---|
| | | 298 K | 653 K | 733 K |
| 1 | $2CH_3CH_2OH \rightarrow 2CH_3CHO + 2H_2$ | — | −9.2 | −25.1 |
| 2 | $2CH_2CHO \rightarrow CH_3CH(OH)CH_2CHO$ | +10.9 | +53.6 | +59.8 |
| 3 | $CH_3CH(OH)CH_2CHO \rightarrow C_3H_5CHO + H2O$ | +4.2 | −87.4 | −98.3 |
| 4a | $C_3H_5CHO + CH_3CH_2OH \rightarrow C_4H_6 + CH_3CHO + H_2O$ | +7.1 | −30.5 | −38.9 |
| 4b | $C_3H_5CHO + H_2 \rightarrow C_4H_6 + H_2O$ | — | −21.3 | −20.9 |
| Overall values for route a[a] | | +22.2 | −73.6 | −102.5 |
| Overall values for route b[b] | | +15.1 | −64.4 | −84.5 |

[a]Steps 1, 2, 3, and 4a.
[b]Steps 1, 2, 3, and 4b.

In some embodiments, a temperature within dehydration reactor 22a or dehydration reactor 22b during reaction of dehydrogenation reactor product stream 16a or dehydration reactor feed stream 16b ranges from 148 to 425° C., or 250 to 500° C., or 275 to 450° C., or 300 to 400° C., or 300 to 350° C., or 300 to 345° C., or 300 to 425° C. In some embodiments, a temperature within dehydration reactor 22a or dehydration reactor 22b during reaction of dehydrogenation reactor product stream 16a or dehydration reactor feed stream 16b may be any reaction temperature as set forth in any of the Tables provided herein, or as utilized in any of the examples described herein.

A pressure in dehydration reactor 22a or dehydration reactor 22b during reaction of dehydrogenation reactor product stream 16a or dehydration reactor feed stream 16b may be greater than 0.1 MPa, from 0.1 MPa to 0.5 MPa, from 0.1 MPa to 0.2 MPa, from 0.3 MPa to 0.6 MPa, from 0.01 MPa to 0.02 MPa, or from 0.01 to 0.6 MPa. In some embodiments, pressure in dehydration reactor 22a or dehydration reactor 22b is at or near atmospheric pressure.

Catalyst Systems

Conversion of ethanol or ethanol and acetaldehyde to form butadiene may occur in the presence of a dehydration catalyst system that contains a Group 4 or Group 5 metal oxide and a support. The dehydration catalyst system may be a heterogeneous catalyst system.

In some embodiments, the dehydration catalyst system may include a support. In certain embodiments, the support is silica ($SiO_2$), including, but not limited to, fumed silica or silicagel. The silica may have a surface area of from 200 to 480 $m^2/g$ or 250 to 380 $m^2/g$, for example. The silica may have a pore size ranging from 50 to 200 Å or 60 Å to 150 Å, for example. The silica may be any silica known to one skilled in the art, such as, for example and without limitation, Aerosil 380 available from Aerosil; DAVISIL® 646 and DAVISIL® 636 available from W. R. Grace and Company; and silica available from Alfa Aesar, as set forth in the examples provided herein.

In some embodiments, the support is MgO, or a magnesia-silica support (MgO/$SiO_2$). A magnesia-silica support may be formed by modifying a silica support with magnesium. For example and without limitation, silica may be mixed with a source of magnesium, such as magnesium hydroxide dissolved in water. After mixing, the mixture may be dried, calcined, and dry milled. The Mg/Si ratio within the magnesia-silica support may be less than 1:1, greater than 2:1, or may range from 1:1 to 2:1. Without being bound by theory, it is believed that the magnesia-silica support contains both basic (magnesia) and acidic (silica) components with different dispersions and locations within the support. Magnesia is believed to activate the aldol condensation reaction and assist in dehydrogenation of ethanol, while silica is believed to catalyze dehydration.

In some embodiments, the support is a zeolite. Zeolites include silicate-based zeolites and amorphous compounds such as faujasite, mordenite, chabazite, offretite, clinoptilolite, erionite, and sihealite, for example. Silicate-based zeolites include alternating $SiO_2$ and $MO_x$ tetrahedra, where M is an element selected from the Groups 1 through 16 of the Periodic Table. The zeolite may have 4-, 6-, 8-, 10-, or 12-membered oxygen ring channels. Examples zeolites that may be used as a support in the process include zeolite A, zeolite L, zeolite beta, X-zeolite, zeolite Y, ZSM-5, MCM-22, and MCM-41. The zeolite may be sodium modified, such as Na—X-zeolite. The zeolite may be potassium modified, such as K—X-zeolite.

In some embodiments, the zeolite is microporous, macroporous, or mesoporous. A microporous zeolite is a zeolite having pores with diameters of less than 2 nm. A mesoporous zeolite is a zeolite having pores with diameters of from 2 to 50 nm. A macroporous zeolite is a zeolite having pores with diameters of greater than 50 or greater than 75 nm. The zeolite may have a crystallite size ranging from 10 to 80 µm, for example.

Without being bound by theory, it is believed that reduced acidity of the support may lead to reduced activity of the dehydration catalyst system for the aldol condensation reaction used for the formation of the crotonaldehyde intermediate, and the subsequent condensation of the intermediate with ethanol to yield the metal complex that leads to butadiene formation. Acidic sites are believed to enhance catalyst activity. Catalyst acidity may be increased by addition of a Lewis acid, such as Zn(II) or Zr (IV). Further, it is believed that more acidic supports form larger amounts of by-products, such as ethene and diethyl ether. Increased Lewis acid strength may lead to direct dehydration of ethanol to yield ethylene and ethyl ether, while decreased acid strength (increased basicity) may lead to reduced activity for condensation reaction leading to the intermediate 3-hydroxybutanal (acetaldol).

Embodiments of the dehydration catalyst system contain a Group 4 or Group 5 metal oxide. For example, the Group 4 metal oxide may be a titanium oxide, zirconium oxide, or hafnium oxide. The Group 5 metal oxide may be a vanadium oxide, niobium oxide, or tantalum oxide, for example.

In some embodiments, the dehydration catalyst system includes a tungsten oxide or a tantalum oxide, which may be supported on a zeolite as described herein.

In certain embodiments, the dehydration catalyst system contains only a single metal oxide. The single metal oxide may be a Group 4 metal oxide, such as a zirconium metal oxide; a Group 5 metal oxide, such as a niobium metal oxide or a tantalum metal oxide; or tungsten oxide. Embodiments that contain only a single metal oxide do not contain additional metal oxides.

In some embodiments, the dehydration catalyst system is a bimetallic catalyst system or a trimetallic catalyst system. As used herein, a "bimetallic catalyst system" is a dehydration catalyst system in which the support is modified with only two metals, and is not modified with additional metals. As used herein, a "trimetallic catalyst system" is a dehydration catalyst system in which the support is modified with only three metals, and is not modified with additional metals. Examples of bimetallic and trimetallic catalyst systems include but are not limited to oxides of: copper-zinc, cobalt-zirconium, cerium-zirconium, zirconium-zinc, and copper-zirconium-zinc. At least one of the two metal oxides in the bimetallic catalyst system may be a Group 4 metal oxide, Group 5 metal oxide, or tungsten oxide. At least one of the three metal oxides in the trimetallic catalyst system may be a Group 4 metal oxide, Group 5 metal oxide, or tungsten oxide. For example and without limitation, bimetallic catalyst systems contain metal oxide including, but not limited to, niobium-rhenium oxides (NbO—ReO), cobalt-zirconium oxides, cerium-zirconium oxides, or zirconium-zinc oxides. Trimetallic catalyst systems contain metal oxides including, but not limited to, copper-zirconium-zinc oxides.

Some specific examples of metal oxides for use herein include, but are not limited to, NbO—ReO, $Ta_2O_5$, Zr—Zn oxides, Zr/Zn/Cu oxides, and tungsten oxides. Some specific examples of metal oxide/support combinations for use herein include, but are not limited to: NbO—ReO supported on silica, NbO—ReO supported on Na—X-zeolite, NbO—ReO supported on K—X-zeolite, $Ta_2O_5$ supported on $SiO_2$, $Ta_2O_5$ supported on Na—X-zeolite, Zr—Zn oxides supported on silica, Zr—Zn oxides supported on magnesia-silica, Zr/Zn/Cu oxides supported on silica, Zr/Zn/Cu oxides supported on magnesia-silica; and tungsten oxide supported on a zeolite.

Each Group 4 metal, Group 5 metal, or tungsten may be present in the dehydration catalyst system in an amount of from about 0.1 to 2 weight percent, or 0.5 to 1.5 weight percent, or 0.5 to 3 weight percent, or 1 weight percent, or any amount provided for in the examples disclosed herein.

The dehydration catalyst system may be prepared by incipient wetness impregnation, also referred to as capillary impregnation or dry impregnation, by techniques known to those skilled in the art. For example and without limitation, the support may be contacted with an aqueous solution of a metal source (e.g., a Group 4 or Group 5 metal source), such as a metal salt. Specific examples of metal sources for use herein include, but are not limited to, ammonium niobate oxalate hydrate, ammonium perrhenate, tantalum chloride salt, zirconium (IV) oxynitrate hydrate ($ZrO(NO_3)_2$), zinc nitrate hydrate ($Zn(NO_3)_2$), and copper acetate monohydrate ($Cu(OAc)_2)_2$).

After impregnation, the support may be dried. For example and without limitation, the support may be dried in air for 12 to 72 hours, or 18 to 36 hours, or 24 hours; dried at an elevated temperature for 3 to 20 hours, or 10 to 15 hours, or 12 hours; or combinations thereof. The elevated temperature may be from 80° C. to 150° C., or any drying temperature used in the examples disclosed herein.

After drying, the support may be calcined. Calcination may convert at least some of the metals deposited by impregnation from metallic form to metal oxides. Calcination may occur at a temperature ranging from 300 to 1050° C., 350 to 900° C., or 450 to 800° C., or 500 to 600° C., or any calcination temperature used in the examples disclosed herein. Calcination may occur in the presence of an inert gas or air. Calcination may occur for a time ranging from 1 to 48 hours, or for any period of time used in the examples as disclosed herein. In some embodiments, the support is extruded or spray dried by techniques known to those skilled in the art. After drying and calcining, the support may be shaped and crushed, such as through a mesh.

In some embodiments, the dehydration catalyst system is made by preparing a slurry of a water-soluble metal salt and support (e.g., silica) in a solvent, followed by evaporation of the solvent and calcination of the support.

Some embodiments of the dehydration catalyst system include a binder, such as alumina. The dehydration catalyst system may also include a porosity agent, such as methyl cellulose and besan.

After a period of use within dehydration reactor 22a or dehydration reactor 22b, coking of the dehydration catalyst system may occur, and the dehydration catalyst system may be subjected to a regeneration cycle. For example and without limitation, the regeneration cycle may be performed in-situ in dehydration reactor 22a or dehydration reactor 22b in the presence of $H_2$ at an elevated temperature, such as 300 to 600° C., or 400° C. to 450° C. The regeneration cycle may optionally be performed in the presence of $H_2$ and moisture.

As used herein, "selectivity of butadiene" in the conversion of ethanol to butadiene by reaction of a stream containing ethanol and acetaldehyde in accordance with the second step of the Ostromislensky process is defined according to the following equation (assuming 92% selectivity to acetaldehyde from ethanol):

$$\text{Selectivity of butadiene (mol \%)} = \frac{\text{Moles of butadiene produced} \times 100}{\text{Moles of ethanol consumed} + \text{Moles of acetaldehyde consumed}/0.92}$$

In some embodiments, the conversion of ethanol to butadiene by reaction of a stream containing ethanol and acetaldehyde in accordance with the second step of the Ostromislensky process exhibits a selectivity of butadiene of from 0.04 mole percent to 80 mole percent, or from 0.5 mole percent to 60 mole percent, or from 5 mole percent to 40 mole percent, or from 10 mole percent to 30 mole percent, or from 15 mole percent to 20 mole percent, or at least 80 mole percent. In some embodiments, the conversion of ethanol to butadiene by reaction of a stream containing ethanol and acetaldehyde in accordance with the second step of the Ostromislensky process exhibits a selectivity of butadiene equal to or greater than any of the discrete selectivities of butadiene provided in the Tables and Examples disclosed herein.

As used herein, "process yield of butadiene" in the conversion of ethanol to butadiene by reaction of a stream containing ethanol and acetaldehyde in accordance with the second step of the Ostromislensky process is defined according to the following equation:

$$\text{Process yield(per-pass) of butadiene (mol \%)} = \frac{\text{Moles of butadiene produced} \times 100}{\text{Total moles of (ethanol} + \text{acetaldehyde)fed}}$$

Is some embodiments, the conversion of ethanol to butadiene by reaction of a stream containing ethanol and acetaldehyde in accordance with the second step of the Ostromislensky process exhibits a process yield of butadiene of from 0.8 to 5 mole percent, or 1 to 4 mole percent, or 2 to 3 mole percent. In some embodiments, the conversion of ethanol to butadiene by reaction of a stream containing ethanol and acetaldehyde in accordance with the second step of the Ostromislensky process exhibits a process yield of butadiene equal to or greater than any of the discrete process yield of butadiene provided in the Tables and Examples disclosed herein.

As used herein, "ethanol efficiency" in the conversion of ethanol to butadiene by reaction of a stream containing ethanol and acetaldehyde in accordance with the second step of the Ostromislensky process is defined according to the following equation:

$$\text{Ethanol efficiency (mol \%)} = \frac{\text{Moles of butadiene produced} \times 100}{\text{Moles of ethanol consumed}}$$

In some embodiments, the conversion of ethanol to butadiene by reaction of a stream containing ethanol and acetaldehyde in accordance with the second step of the Ostromislensky process exhibits an ethanol efficiency of from 0.04 to 70 mole percent, or from 1 to 50 mole percent, or from 5 to 40 mole percent, or from 20 to 30 mole percent. In some embodiments, the conversion of ethanol to butadiene by reaction of a stream containing ethanol and acetaldehyde in accordance with the second step of the Ostromislensky process exhibits an ethanol efficiency equal to or greater than any of the discrete ethanol efficiencies provided in the Tables and Examples disclosed herein.

As used herein, "acetaldehyde efficiency" in the conversion of ethanol to butadiene by reaction of a stream containing ethanol and acetaldehyde in accordance with the second step of the Ostromislensky process is defined according to the following equation:

$$\text{Acetaldehyde efficiency (mol \%)} = \frac{\text{Moles of butadiene produced} \times 100}{\text{Moles of acetaldehyde consumed}}$$

In some embodiments, the conversion of ethanol to butadiene by reaction of a stream containing ethanol and acetaldehyde in accordance with the second step of the Ostromislensky process exhibits an acetaldehyde efficiency of from 0.05 mole percent to 335 mole percent, or from 0.5 mole percent to 200 mole percent, or from 1 mole percent to 100 mole percent, or from 10 mole percent to 50 mole percent, or from 15 mole percent to 35 mole percent. In some embodiments, the conversion of ethanol to butadiene by reaction of a stream containing ethanol and acetaldehyde in accordance with the second step of the Ostromislensky process exhibits an acetaldehyde efficiency equal to or greater than any of the discrete acetaldehyde efficiencies provided in the Tables and Examples disclosed herein.

As used herein "ethanol conversion" refers to the weight percentage of ethanol in a feedstream that undergoes conversion to butadiene during reaction of the feedstream, which contains ethanol and acetaldehyde, in accordance with the second step of the Ostromislensky process. In some embodiments, the conversion of ethanol to butadiene by reaction of a stream containing ethanol and acetaldehyde in accordance with the second step of the Ostromislensky process exhibits an ethanol conversion of from 5 weight percent to 60 weight percent, or from 10 weight percent to 50 weight percent, or from 15 weight percent to 40 weight percent, or from 20 weight percent to 30 weight percent, or at least 50 weight percent. In some embodiments, the conversion of ethanol to butadiene by reaction of a stream containing ethanol and acetaldehyde in accordance with the second step of the Ostromislensky process exhibits an ethanol conversion equal to or greater than any of the discrete ethanol conversions provided in the Tables and Examples disclosed herein.

As used herein "acetaldehyde conversion" refers to the weight percentage of acetaldehyde in a feedstream that undergoes conversion to butadiene during reaction of the feedstream, which contains ethanol and acetaldehyde, in accordance with the second step of the Ostromislensky process. In some embodiments, the conversion of ethanol to butadiene by reaction of a stream containing ethanol and acetaldehyde in accordance with the second step of the Ostromislensky process exhibits an acetaldehyde conversion of from 15 to 95 weight percent, or from 25 to 85 weight percent, or from 35 to 75 weight percent, or from 45 to 65 weight percent. In some embodiments, the conversion of ethanol to butadiene by reaction of a stream containing ethanol and acetaldehyde in accordance with the second step of the Ostromislensky process exhibits an acetaldehyde conversion equal to or greater than any of the discrete acetaldehyde conversions provided in the Tables and Examples disclosed herein.

EXAMPLES

The disclosure having been generally described, the following examples show particular embodiments of the disclosure. It is understood that the example is given by way of illustration and is not intended to limit the specification or the claims. All compositions percentages given in the examples are by weight.

In the Examples provided below, various dehydration catalyst systems are tested for use in the second step of the two-step Ostromislensky process for conversion of a stream containing ethanol and acetaldehyde to butadiene.

Catalyst Preparation

Example A—Preparation of NbO—ReO Supported on Silica

A dehydration catalyst system containing 2 weight percent Nb and 0.1 weight percent Re was prepared based on a silica support having a surface area of 380 m$^2$/g, available from Aerosil as Aerosil 380. The silica support was subjected to incipient wetness impregnation with a 99% pure aqueous solution of ammonium niobate oxalate hydrate, and a 99.9% pure aqueous solution of ammonium perrhenate, both available from Aldrich. After impregnation, the silica support was dried in air for 24 hours, then dried at 120° C. for 12 hours, and then calcined at 520° C. for 3.5 hours.

Example B—Preparation of NbO—ReO Supported on Zeolite

The influence of basicity of support was tested by preparation of dehydration catalyst systems containing 2 weight percent of Nb and 0.1 weight percent of Re supported on an extrudate of Na—X-zeolite, and preparation of dehydration catalyst systems containing 2 weight percent of Nb and 0.1 weight percent of Re supported on an extrudate of K—X-zeolite. These dehydration catalyst systems were prepared from Nb and Re salts using 1/16$^{th}$ inch extrudates of Na—X-faujasites and K—X-faujasites by dry impregnation. The Na—X-faujasite extrudates were prepared with: SILIPO-RITE® G5-XP, which is a molecular sieve having a 13X crystal structure and a Si/Al atomic ratio 1/1.5, available from CHS; CATAPAL® C1, which is an alumina binder available from Sasol Chemicals; and methyl cellulose and besan as a porosity agent. K-LSX zeolite (potassium modified, low silica X-zeolite) was used as the starting zeolite for preparing the K—X-faujasite extrudate. Ammonium niobate oxalate hydrate and ammonium perrhenate salt solution was used to co-impregnate both Nb and Re into the zeolites of the respective dehydration catalyst systems. After impregnation, niobium and rhenium oxides were obtained on the Na—X-faujasites and K—X-faujasites following calcinations at 550° C.

Example C—Preparation of Ta$_2$O$_5$ Supported on Silica or Zeolite

A tantalum oxide (Ta$_2$O$_5$/SiO$_2$) catalyst evaluation was performed. A Ta-based dehydration catalyst system was prepared from tantalum chloride salt and a silica support by dry impregnation. The silica support was DAVISIL® 646 having a pore size of 150 Å, available from W. R. Grace and Company. An additional Ta-based dehydration catalyst system was prepared from tantalum chloride salt and a Na—X-zeolite support by dry impregnation. Tantalum chloride was dissolved in ethanol and the solution was used for the impregnation of the silica and Na—X-extrudate supports, respectively. After impregnation, the supports were dried for 24 hours to remove ethanol, then the dehydration catalyst systems were dried in an oven at 150° C. for 6 hours followed by calcination at 350° C. for 1 hour, followed by a final calcination at 450° C. for 4 hours. After cooling, the dehydration catalyst systems were pressed into tablets and crushed to 40-60 mesh. Both Ta$_2$O$_5$ dehydration catalyst systems contained 2 weight percent of Ta.

Example D—Preparation of Zr/Zn Oxide Supported on Silica

Two different dehydration catalyst systems containing 1.5 weight percent Zr and 0.5 weight percent Zn were prepared from Zr and Zn salts using one of two different silica supports. The two silica supports were DAVISIL® 636 having a pore size of 60 Å, and DAVISIL® 646 having a pore size of 150 Å, both available from W. R. Grace and Company. The dehydration catalyst systems were prepared by wet impregnation. Zirconium (IV) oxynitrate hydrate (ZrO(NO$_3$)$_2$) and zinc nitrate hydrate (Zn(NO$_3$)$_2$) salt solutions in water were used for the co-impregnation of the respective silica supports. After drying for 72 hours to remove excess water, the catalysts were dried in an oven at 80° C. for 3 hours, followed by calcinations at 500° C. for 5 hours. After cooling, the dehydration catalyst systems were pressed into tablets and crushed to 40-60 mesh. An influence of the pore size of the silica support on the process chemistry was evaluated by using the two different pore sizes, 60 Å and 150 Å. Influence of promoter composition was investigated by preparation of a third dehydration catalyst system prepared by the same method using DAVISIL® 646, but containing 3 weight percent Zr and 0.5 weight percent Zn.

Example E—Preparation of Zr/Zn Oxide Supported on MgO/SiO$_2$

A dehydration catalyst system containing an oxide of Zr—Zn supported a magnesia-silica (MgSiO$_2$) was prepared by adding Zr and Zn salts to the magnesia-silica support by wet impregnation. The magnesia-silica support was prepared by dissolving silica and 15 weight percent magnesium hydroxide in water. The solution was mixed, dried, and then calcined at 550° C. The silica included DAVISIL® 636 or DAVISIL® 646. The Zr and Zn salts used to impregnate the magnesia-silica support were salt solutions in water, and contained zirconium (IV) oxynitrate hydrate ($ZrO(NO_3)_2$) and zinc nitrate hydrate ($Zn(NO_3)_2$). After impregnation, the support was dried for 72 hours to remove excess water, then the catalyst was dried in an oven at 80° C. for 3 hours, followed by calcination at 500° C. for 5 hours. After cooling, the dehydration catalyst system was pressed into tablets and crushed to 40-60 mesh.

Example F—Preparation of Zr/Zn/Cu Oxide Supported on $SiO_2$

A tri-metallic dehydration catalyst system containing an oxide of Zr/Zn/Cu was prepared. The dehydration catalyst system contained 1 weight percent Zr, 1 weight percent Zn, and 1 weight percent Cu. A salt solution in water of zirconium (IV) oxynitrate hydrate ($ZrO(NO_3)_2$), zinc nitrate hydrate ($Zn(NO_3)_2$) and copper acetate monohydrate ($Cu(OAc_2)_2$) was used for the wet co-impregnation of the silica support. The silica was DAVISIL® 636. After drying the support to remove excess water for 72 hours, the dehydration catalyst system was dried in an oven at 80° C. for 3 hours, followed by calcination at 500° C. for 5 hours. After cooling, the dehydration catalyst system was pressed into tablets and crushed to 40-60 mesh.

Example G—Varying Mg/Si Molar Ratio

Dehydration catalyst systems containing Zr/Zn or Zr/Zn/Cu oxide supported on $MgO/SiO_2$ were prepared with varying Mg/Si molar ratios as follows. $MgO/SiO_2$ supports were prepared at different Mg/Si molar ratios, 1:1 and 2:1. The $MgO/SiO_2$ supports were prepared by dry mulling for 2 hours followed by wet impregnation. For preparation of the dehydration catalyst systems, an $MgO/SiO_2$ having an Mg/Si molar ratio of 1:1 and an $MgO/SiO_2$ having an Mg/Si molar ratio of 2:1 were each impregnated with the bimetallic oxide Zr/Zn, and each contained 1.5 weight percent Zr and 0.5 weight percent Zn. Also, an $MgO/SiO_2$ having an Mg/Si molar ratio of 1:1 and an $MgO/SiO_2$ having an Mg/Si molar ratio of 2:1 were each impregnated with the trimetallic oxide Zr/Zn/Cu, and each contained 1 weight percent Zr, 1 weight percent Zn, and 1 weight percent Cu.

Experimental Set-Up for Each of Examples 1-15

Figure 4:
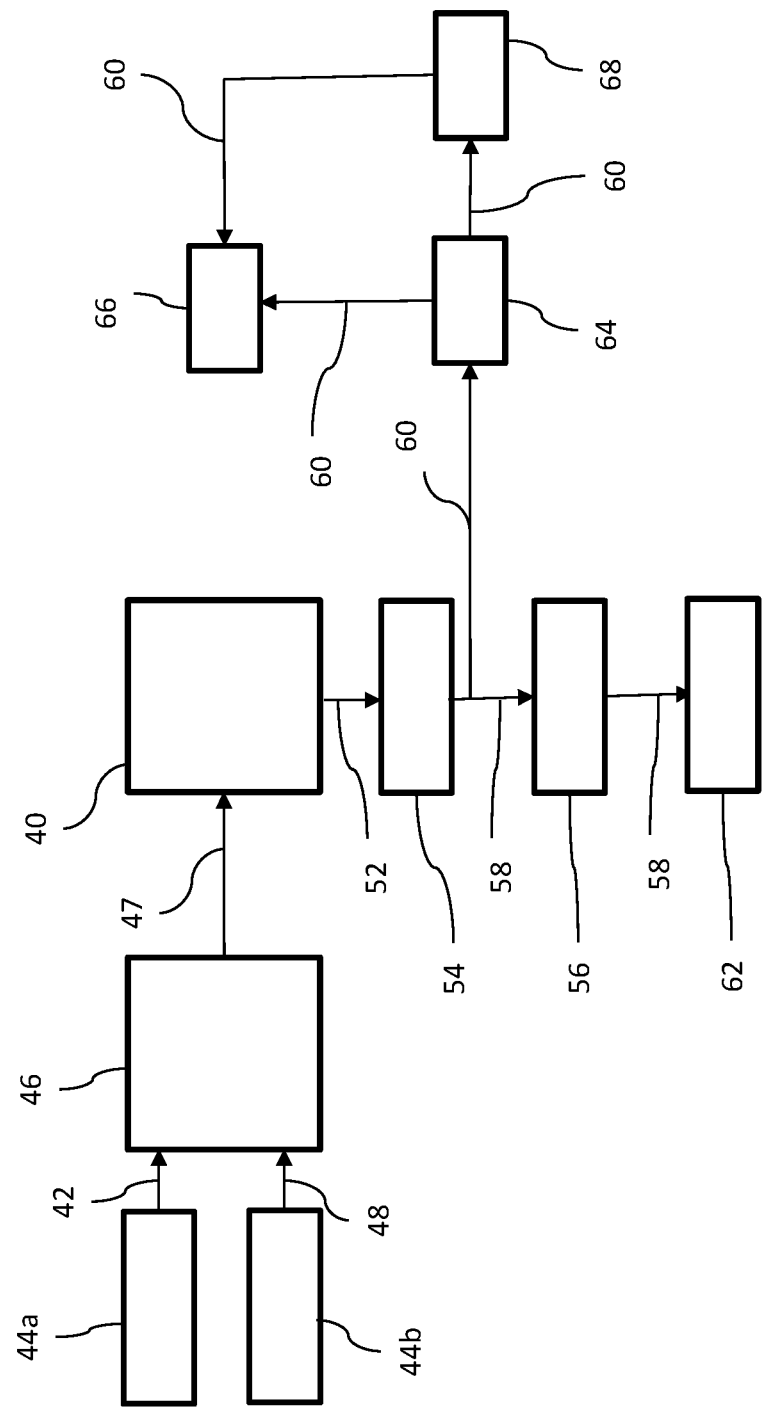
FIG. 4 depicts the process scheme used in the examples provided herein.

The experimental set-up used in each of Examples 1-15 is illustrated in FIG. 4. Dehydration reactor 40 was a fixed bed continuous upstream flow reactor having a ¼" internal diameter (ID). Dehydration reactor 40 was heated in a four zone furnace. In each of Examples 1-15, the respective dehydration catalyst system was loaded in a 3.5" catalyst zone in the middle of dehydration reactor 40, between two zones of silicium carbide (SiC, 200-450 mesh particle size, available from Aldrich).

Hydrous ethanol 42 fed to dehydration reactor 40 included 190 proof ethanol (95 weight percent ethanol, 5 weight percent water), and acetaldehyde 48 fed to dehydration reactor 40 was 99.99% pure acetaldehyde available from Aldrich. Prior to being fed to dehydration reactor 40, hydrous ethanol 42 and acetaldehyde 48 were fed to static mixer 46 from helium pressurized feed cans using liquid mass flow controllers 44a and 44b to control flow. Acetaldehyde 48 was maintained at 2° C. to avoid decomposition.

The hydrous ethanol 42 and acetaldehyde 48 left static mixer 46 and entered dehydration reactor 40 as combined feed 47 at reaction conditions.

Effluent 52 from dehydration reactor 40 flows through effluent condenser 54 and liquid separator 56 downstream of dehydration reactor 40 for separation of liquid effluent 58 and gaseous effluent 60 from dehydration reactor 40. After separation, liquid effluent 58 was analyzed in an Agilent 6290 gas chromatography system 62 using an HP wax column. The carrier gas used in the Agilent 6290 gas chromatography system 62 was helium. A wet test meter (WTM) 64 was used to measure the gas phase flow before sending the gaseous effluent 60 either directly to gas analyzer 66 or to gas bag sample 68 and subsequently to gas analyzer 66. Gas analyzer 66 was an Agilent Refinery Gas Analyzer. The carrier gas used in the gas analyzer 66 was helium and $N_2$. The butadiene observed to be primarily present in the gaseous effluent 60, and unreacted ethanol/acetaldehyde and other oxygenates were observed to be primarily present in the liquid effluent 58.

In each of Examples 1-15, samples of the combined feed 47 were collected at the beginning of the respective experimental run, liquid effluent 58 and off-gas samples of gaseous effluent 60 were obtained after the reaction in dehydration reactor 40 was started, and the effluent rate was measured. Nitrogen was used as a co-feed with acetaldehyde 48 and hydrous ethanol 42, and a net gas effluent rate was calculated.

In each of Examples 1-15, liquid effluent 58 from dehydration reactor 40 was analyzed for the presence of ethanol, acetaldehyde, butadiene, diethylether and other oxygenates on Agilent 6290 GC system 62 using a HP wax column. Butanol was used as an internal standard to provide for accurate analysis of liquid effluent 58 due to the water content and shifting baseline. Gaseous effluent 60, including butadiene, ethylene and other $C_4$ and lighter components, were analyzed using gas analyzer 66 (Refinery Gas Analyzer (RGA) from Agilent), either using gas bag sample 68 or by diverting gaseous effluent 60 to gas analyzer 66 after measuring an effluent rate. Conversions of ethanol and acetaldehyde were calculated from the analysis of the combined feed 47 using Agilent 6290 GC system 62 using a HP wax column and analysis of liquid effluent 58 and gaseous effluent 60.

A regeneration cycle in-situ was performed at the end of each experimental run with $H_2$ overnight at 450° C. The Nb—Re bimetallic oxide catalysts were activated overnight at 400° C. with hydrogen in the presence of moisture. The Zr—Zn bimetallic oxide catalysts were activated at 300° C. with hydrogen.

Table 2 shows the range of operating conditions used during Examples 1-15. The tests were mostly carried out at atmospheric pressures, but some tests were conducted for investigating the effect of pressure on butadiene yields, as detailed below.

TABLE 2

| Parameter | Range |
| --- | --- |
| Temperature, ° C. | 300-425 |
| Pressure, psig | 2-4[a], and 50-80[b] |
| LHSV, hr$^{-1}$ | 0.3-0.5[a], and 1-5[b] |
| Ethanol/acetaldehyde, volumetric ratio | 9:1-1:0 |

In Table 2, the pressure and LHSV marked with "a" were used in conjunction, and the pressure and LHSV marked with "b" were used in conjunction.

Example 1

Experimental runs were performed utilizing the experimental set-up depicted in FIG. 4 on the following dehydration catalyst systems: an Nb(2 wt. %)/Re(0.1 wt. %) catalyst supported on silica prepared in accordance with Example A; an Nb(2 wt. %)/Re(0.1 wt. %) supported on an Na X zeolite prepared in accordance with Example B; an Nb(2 wt. %)/Re(0.1 wt. %) supported on an K X zeolite prepared in accordance with Example B; a $Ta_2O_5$ supported on silica prepared in accordance with Example C; a $Ta_2O_5$ supported on Na X zeolite prepared in accordance with Example C; a Zr/Zn (1.5 wt. %/0.5 wt. %) supported on silica (150 Å) prepared in accordance with Example D; a Zr/Zn (3.0 wt. %/0.5 wt. %) supported on silica (150 Å) prepared in accordance with Example D; and a Zr/Zn/Cu (1 wt. %/1 wt. %/1 wt. %) supported on silica prepared in accordance with Example F. The temperature, LHSV, ethanol conversion, acetaldehyde conversion, butadiene conversion, ethanol efficiency, and acetaldehyde efficiency for experimental runs are shown in Table 3.

percent and ethylene content of 46 mole percent in the gaseous effluent. At a reactor temperature of 315° C., the butadiene content in the gaseous effluent was 3.4 mole percent and the ethylene content was 43 mole percent. As shown in Table 3, at a reactor temperature of 325° C. and an LHSV of 0.31 $hr^{-1}$, the butadiene selectivity was 0.64 mole percent at a 23% ethanol conversion and 86% acetaldehyde conversion. Hydrogen was observed in the gaseous effluent, which may indicate the dehydrogenation of ethanol to form acetaldehyde, and insufficient aldol condensation to form crotonaldehyde to react further with ethanol. The presence of ethylene in the gaseous effluent may indicate catalytic activity for dehydration of ethanol, which may be due to acid active sites on the silica support. Without being bound by theory, a reduction in the acidic active sites by use of a more basic support may reduce selectivity to ethylene.

Example 3

Experimental runs were conducted with a 2 weight percent Ta-oxide supported on a silica support. The 2 weight

TABLE 3

| | Catalyst | | | | | | | |
|---|---|---|---|---|---|---|---|---|
| | Nb/Re on silica | Nb/Re on Na X zeolite | Nb/Re on K X zeolite | Ta on silica | Ta on Na X zeolite | Zr/Zn on silica (1.5%/0.5%) | Zr/Zn on silica (3%/0.5%) | Zr/Zn/Cu on silica |
| Temperature, ° C. | 325 | 340 | 315 | 325 | 325 | 400 | 400 | 400 |
| LHSV, $hr^{-1}$ | 0.31 | 0.31 | 0.31 | 0.31 | 0.39 | 0.49 | 0.49 | 0.49 |
| Ethanol conversion, wt. % | 23.20 | 16.93 | 9.10 | 25.38 | 30.40 | 41.98 | 54.54 | 22.25 |
| Acetaldehyde conversion, wt. % | 86.44 | 82.84 | 63.12 | 73.26 | 53.69 | 52.09 | 56.17 | 17.04 |
| Butadiene Selectivity, mol. % | 0.64 | 0.51 | 0.05 | 19.13 | 5.30 | 28.12 | 34.50 | 54.00 |
| Ethanol efficiency, mol. % | 0.96 | 0.93 | 0.05 | 45.89 | 7.96 | 37.98 | 42.59 | 65.14 |
| Acetaldehyde efficiency, mol. % | 0.52 | 0.39 | 0.06 | 35.66 | 17.32 | 117.72 | 198.27 | 334.79 |

Figure 5:
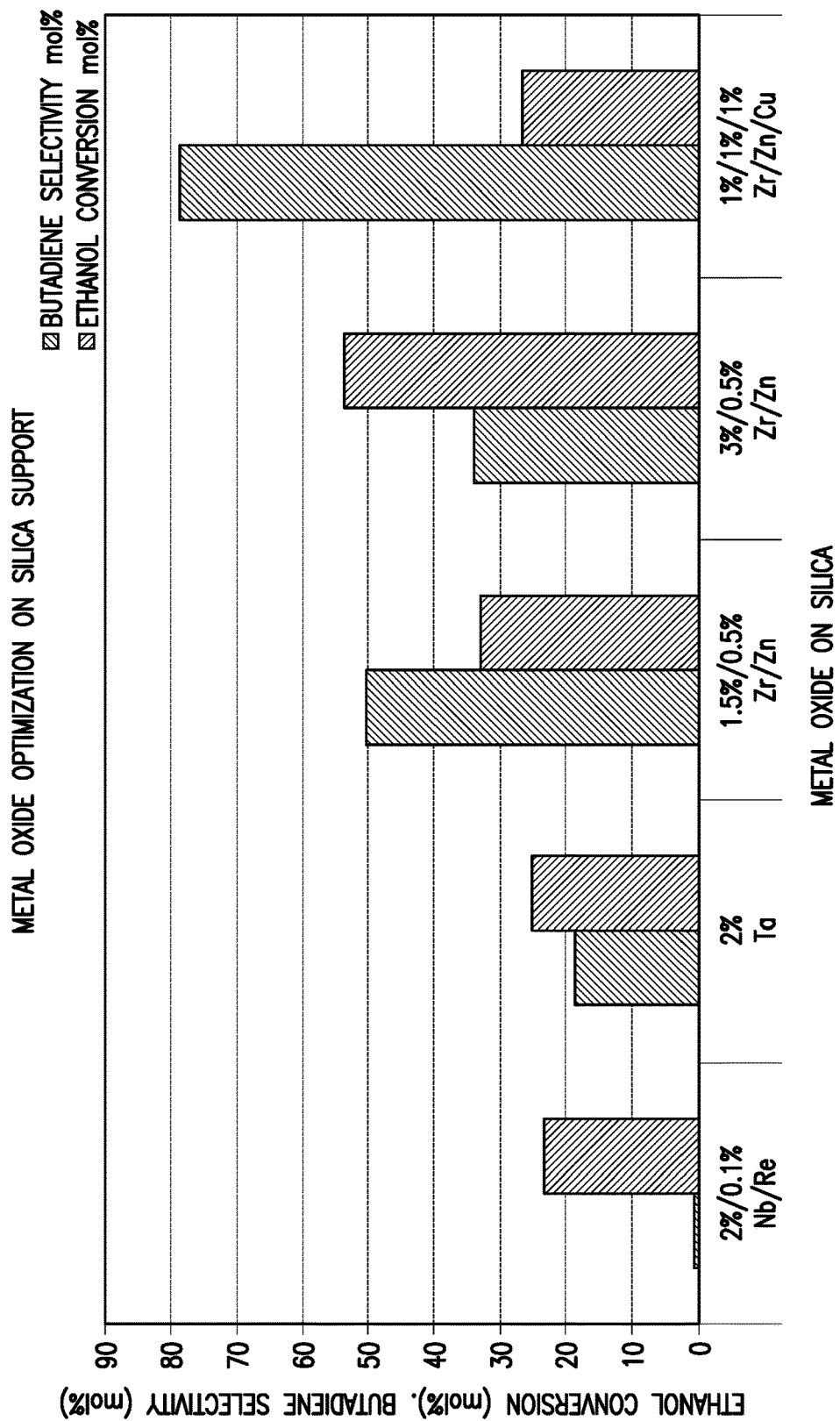
FIG. 5 is a bar graph comparison of ethanol conversion and butadiene selectivity on various $SiO_2$ supported dehydration catalyst systems.

FIG. 5 shows butadiene selectivity (mol. %) and ethanol conversion (mol. %) for the following dehydration catalyst systems: an Nb(2 wt. %)/Re(0.1 wt. %) catalyst supported on silica prepared in accordance with Example A; a $Ta_2O_5$ supported on silica prepared in accordance with Example C; a Zr/Zn (1.5 wt. %/0.5 wt. %) supported on silica (150 Å) prepared in accordance with Example D; a Zr/Zn (3.0 wt. %/0.5 wt. %) supported on silica (150 Å) prepared in accordance with Example D; and a Zr/Zn/Cu (1 wt. %/1 wt. %/1 wt. %) supported on silica prepared in accordance with Example F.

Example 2

A Nb(2 wt. %)/Re(0.1 wt. %) metal oxide catalyst supported on $SiO_2$ prepared in accordance with Example A was evaluated for butadiene production utilizing the experimental set-up illustrated in FIG. 4 and discussed above. Experimental runs utilizing the Nb(2 wt. %)/Re(0.1 wt. %) metal oxide catalyst supported on $SiO_2$ were repeated at reactor temperature conditions of 300-350° C. at different space velocities. Results from the experimental runs at 350° C. and an LHSV of 0.39 $hr^{-1}$ showed a butadiene content of 6 mole percent Ta-oxide supported on a silica support was prepared in accordance with Example C. The experimental runs were conducted utilizing the experimental set-up illustrated in FIG. 4 and discussed above. The results are presented in Table 4. The highest yields of butadiene were obtained at an ethanol:acetaldehyde volumetric ratio of 0.7:0.3, a temperature of 325° C., and an LHSV of 0.4 $hr^{-1}$. Increase or decrease of temperature reduced the butadiene yield relative to a temperature of 325° C.

TABLE 4

Results of catalyst evaluation of ethanol:acetaldehyde over Ta (2%) on silica (150 Å) support at different temperatures and space velocities and 5 psig pressure
Catalyst - 2% Ta on silica (150 Å)

| Ethanol: Acetaldehyde Volumetric ratio | Temperature, ° C. | LHSV, $hr^{-1}$ | Ethanol conversion, wt. % | Acetaldehyde conversion, wt. % | Butadiene Selectivity, mol. % | Butadiene Yield, mol. % |
|---|---|---|---|---|---|---|
| 0.7:0.3 | 325 | 0.4 | 25.38 | 73.26 | 19.1 | 8.1 |
| 0.7:0.3 | 340 | 0.4 | 30.33 | 87.84 | 15.6 | 7.9 |

TABLE 4-continued

Results of catalyst evaluation of ethanol:acetaldehyde over Ta (2%)
on silica (150 Å) support at different temperatures and
space velocities and 5 psig pressure
Catalyst - 2% Ta on silica (150 Å)

| Ethanol: Acetaldehyde Volumetric ratio | Temperature, °C. | LHSV, hr$^{-1}$ | Ethanol conversion, wt. % | Acetaldehyde conversion, wt. % | Butadiene Selectivity, mol. % | Butadiene Yield, mol. % |
|---|---|---|---|---|---|---|
| 0.7:0.3 | 315 | 0.4 | 27.50 | 71.25 | 11.6 | 5.0 |
| 0.8:0.2 | 325 | 0.4 | 18.32 | 77.26 | 14.0 | 4.5 |
| 0.8:0.2 | 325 | 1.36 | 20.72 | 61.01 | 12.5 | 3.6 |
| 0.9:0.1 | 325 | 0.40 | 23.50 | 31.78 | 6.7 | 7.7 |
| 0.9:0.1 | 340 | 0.40 | 23.09 | 29.61 | 9.4 | 2.1 |

With reference to Table 4, higher conversions were observed as the temperature was increased, but reduced butadiene selectivity was also observed.

Example 4

Zr/Zn bimetallic catalysts were supported on SiO$_2$ of different pore sizes to demonstrate the effect of support pore size on the conversion of ethanol to butadiene. The Zr/Zn bimetallic catalysts supported on SiO$_2$ were prepared in accordance with Example D. Experimental runs utilizing the experimental set-up depicted in FIG. 4 were performed using Zr (1.5 wt. %)/Zn (0.5 wt. %) on silica (150 Å) at different ethanol/acetaldehyde feed compositions with volumetric ratios of ethanol to acetaldehyde ranging from 0.8:0.2 to 0.2:0.8, and temperatures ranging from 300-345° C. Table 5 shows the results. The results from the experimental runs indicate selectivity to butadiene on the SiO$_2$ supported Zr—Zn catalysts in the gaseous effluent at the space velocities and feed compositions tested. The gaseous effluent was predominantly butadiene with some ethylene or CO or CO$_2$. The liquid effluent contained some oxygenates, some of which were identified as ethoxy ethane, ethoxy butane, diethoxy ethane, ethoxy butane and 2-butenal using GC-MS. The results indicated that the presence of acetaldehyde increases yields of butadiene. However, excess acetaldehyde proved to be detrimental to the formation of butadiene over the Zr—Zn catalysts on silica supports. The maximum selectivity of butadiene was observed at a volumetric ratio of ethanol:acetaldehyde of 0.8:0.2, a temperature of 325° C., 21.7% ethanol conversion, and 52.7% acetaldehyde conversion.

TABLE 5

Results of catalyst evaluation of ethanol:acetaldehyde over Zr—Zn
(1.5%-0.5%) on silica (150 Å) support at 325° C. and 5 psig
Catalyst - 1.5% Zr—0.5% Zn on silica (150 Å)

| Ethanol: Acetaldehyde Volumetric ratio | LHSV, hr$^{-1}$ | Ethanol conversion, wt. % | Acetaldehyde conversion, wt. % | Butadiene Selectivity, mol. % | Butadiene Yield, mol. % |
|---|---|---|---|---|---|
| 0.8:0.2 | 0.4 | 13.2 | 71.0 | 11.3 | 3.0 |
| 0.6:0.4 | 0.4 | 31.3 | 70.5 | 7.1 | 3.6 |
| 0.5:0.5 | 0.4 | 35.2 | 62.0 | 5.5 | 2.8 |
| 0.4:0.6 | 0.4 | 42.3 | 55.2 | 5.4 | 2.8 |
| 0.8:0.2 | 0.4 | 21.7 | 52.7 | 13.8 | 4 |
| 0.4:0.1 | 0.38 | 29.7 | 55.0 | 12.8 | 4.6 |
| 1.5:0.3 | 0.42 | 10.5 | 42.4 | 11.8 | 2.1 |
| 2.0:0.5 | 0.45 | 12.9 | 42.7 | 4.3 | 0.85 |

The results demonstrate that Zr—Zn supported on silica yields butadiene in the gaseous effluent. Without being bound by theory, the formation of crotonaldehyde or 2-butenal is believed to be the intermediate step in the reaction process. The acidity of the support of the catalyst system is believed to affect the steps in the reaction mechanism. An increase in acidity of the support is believed to yield direct dehydration of the ethanol to ethylene and formation of other oxygenate molecules, such as diethyl ether. Without being bound by theory, the presence of excess ethanol by volume in comparison to acetaldehyde is believed to provide larger yields of butadiene to allow the reaction of crotonaldehyde with ethanol to proceed. A decrease in acidity of the support is believed to lead to a reduced activity of the catalyst system for the aldol condensation reaction required for the formation of the crotonaldehyde intermediate and the subsequent condensation of the intermediate with ethanol to yield the metal complex that leads to butadiene formation.

Example 5

Zr/Zn bimetallic catalysts supported on SiO$_2$ (60 Å) were prepared in accordance with Example D. The series of experimental runs utilizing the experimental set-up shown in FIG. 4 and using the Zr—Zn (1.5%-0.5%) on silica (60 Å) catalyst resulted in a highest butadiene selectivity of 28 wt % at a 9% conversion of ethanol, a temperature of 325° C., an LHSV of 0.4 hr$^{-1}$, and an ethanol-acetaldehyde volumetric ratio of 4:1. Ethanol efficiency was calculated at 78%. Butadiene selectivity was reduced to 15% with an increased ethanol conversion of 28% at a temperature of 340° C. Increasing the space velocity at a constant temperature also gave higher ethanol conversion at lower butadiene selectivity. The influence of the silica pore size on the butadiene selectivity, as demonstrated by comparing the results obtained using the Zr/Zn bimetallic catalysts supported on SiO$_2$ (150 Å) with the results obtained using the Zr/Zn bimetallic catalysts supported on SiO$_2$ (60 Å), indicates differences on the catalyst surface with smaller pore size.

Example 6

The influence of metal content was evaluated by the preparation of a Zr (3 wt. %)/Zn (0.5 wt. %) catalyst supported on silica (60 Å) in accordance with Example D. A series of experimental runs utilizing the experimental set-up shown in FIG. 4 and using the Zr (1.5 wt. %)/Zn (0.5 wt. %) on silica (60 Å) support as the catalyst system resulted in a highest butadiene selectivity of 28% at a 42% conversion of ethanol, a temperature of 400° C., an LHSV of 0.48 hr$^{-1}$, and an ethanol-acetaldehyde volumetric ratio of 4:1. The butadiene selectivity was reduced to 24% with ethanol conversion of 37% at 400° C. and with a 50:50 volumetric mix of ethanol and acetaldehyde. Increasing the space velocity to 1.9 hr$^{-1}$ at a constant temperature of 400° C. resulted in an ethanol conversion of 41% at a butadiene selectivity of 21%. An increase in hydrogen and ethylene production was observed in the gaseous effluent at a temperature of 400° C. compared to the hydrogen and ethylene production observed in the gaseous effluent at a temperature of 325° C. The butadiene composition of the gaseous effluent decreased from greater than 80 weight % at a temperature of 325° C. to about 45 weight % at a temperature of 400° C., but the accompanied increased production rate of butadiene led to an overall increase in butadiene selectivity of the feed converted.

Experimental runs using the Zr (3 wt. %)/Zn (0.5 wt. %) catalyst supported on silica (60 Å pore size) resulted in a highest butadiene selectivity of 41% at 25% conversion of ethanol, a temperature of 400° C., an LHSV of 0.52 hr$^{-1}$, and an ethanol-acetaldehyde volumetric ratio of 4:1. The butadiene selectivity was reduced to 37% with an ethanol conversion of 35% at a temperature of 400° C., and an LHSV of 0.5 hr$^{-1}$. The butadiene selectivity was reduced to 35% at 55% ethanol conversion, a temperature of 400° C., and an LHSV of 0.48 hr$^{-1}$.

While not being bound by theory, it is believed that ZnO is catalytically active for the dehydrogenation of ethanol. The silica support and/or a combination of the Lewis acidic metal centers may catalyze the subsequent aldol condensation of ethanol and acetaldehyde. $ZrO_2$ may catalyze the Meerwein-Ponndorf-Verley reduction of acetaldol. The ethylene concentration in the gaseous effluent was increased for the Zr (3 wt. %)/Zn (0.5 wt. %) catalyst supported on silica (60 Å pore size) in comparison to that obtained using the Zr (1.5 wt. %)/Zn (0.5 wt. %) supported on silica under the same conditions. While not being bound by theory, the increase in ethylene concentration in the gaseous effluent may be due to the increase in Lewis acidity of the catalyst, which may favor side products.

Example 7

Experimental runs utilizing the experimental set-up shown in FIG. 4 and using the Zr (1 wt. %)/Zn (1 wt. %)/Cu (1 wt. %) supported on DAVISIL® 636 (60 Å) prepared in accordance with Example F were conducted. An experimental run in which the temperature was 400° C., the LHSV was 0.48 hr$^{-1}$, and the feed did not contain any acetaldehyde yielded a butadiene selectivity of 59% at a 21% ethanol conversion. With a 4:1 volumetric ratio of ethanol to acetaldehyde in the feed, a temperature of 400° C., and an LHSV of 0.48 hr$^{-1}$, a butadiene selectivity of 54% was obtained at a 22% ethanol conversion and 17% acetaldehyde conversion. A maximum butadiene selectivity of 75% was observed at 11% ethanol conversion, 14% acetaldehyde conversion, a temperature of 400° C., an LHSV of 0.5 hr$^{-1}$, and a 4:1 ethanol to acetaldehyde volumetric ratio in feed.

Addition of acetaldehyde to the feed did not provide higher butadiene selectivity with Zr (1 wt. %)/Zn (1 wt. %)/Cu (1 wt. %) supported on DAVISIL® 636 (60 Å). While not being bound by theory, this may be due to the fact that the Cu/Zr/Zn silica supported catalyst produces acetaldehyde with pure ethanol.

Without being bound by theory, it is believed that the degree of acidity in the support affects reaction steps that are acid catalyzed. It is believed that more acidic supports form larger amounts of the by-products ethene and diethyl ether. Both Zn(II) and Zr(IV) are Lewis acidic and may enhance this catalyst activity. Thermal programmed desorption (TPD) evaluations of the Cu/Zr/Zn silica supported catalysts may be used to generate data on the acidic-basic nature of the catalyst systems.

Example 8

Experimental runs utilizing the experimental set-up shown in FIG. 4 were performed using the bimetallic Zr/Zn (1.5 wt. %/0.5 wt. %) on silica (60 Å) prepared in accordance with Example D and the trimetallic Zr/Zn/Cu (1 wt %/1 wt %/1 wt %) on silica (60 Å) prepared in accordance with Example F, and results for each are shown in Tables 6 and 7, respectively.

TABLE 6

Results of catalyst evaluation of ethanol:acetaldehyde over Zr—Zn (1.5%-0.5%) on silica (60 Å) support at 400° C.

| Catalyst - Zr/Zn on silica (1.5%/0.5%) | Day 1 | | | | Day 2 | | | |
|---|---|---|---|---|---|---|---|---|
| | Time = 60 min. | Time = 120 min. | Time = 180 min. | Time Average | Time = 60 min. | Time = 120 min. | Time = 180 min. | Time Average |
| Temperature, ° C. | 400 | 400 | 400 | 400 | 400 | 400 | 400 | 400 |
| LHSV, hr$^{-1}$ | 0.48 | 0.48 | 0.48 | 0.48 | 0.48 | 0.48 | 0.48 | 0.48 |
| Ethanlol:Acetaldehyde volumetric ratio | 4 | 4 | 4 | 4 | 4 | 4 | 4 | 4 |
| Ethanol conversion, wt. % | 49.55 | 17.42 | 31.72 | 32.90 | 34.91 | 45.34 | 39.15 | 39.80 |
| Acetaldehyde conversion, wt. % | 60.24 | 43.52 | 51.96 | 51.91 | 65.62 | 52.34 | 43.02 | 53.66 |
| Butadiene selectivity, mol. % | 34.26 | 76.67 | 40.68 | 50.54 | 37.65 | 35.61 | 40.54 | 37.93 |
| Ethanol efficiency, mol. % | 47.40 | 137.15 | 62.92 | 82.49 | 60.90 | 49.30 | 53.70 | 54.63 |
| Acetaldehyde efficiency, mol. % | 134.39 | 188.98 | 125.08 | 149.49 | 107.19 | 139.43 | 179.75 | 142.12 |

TABLE 7

Results of catalyst evaluation of ethanol:acetaldehyde over Zr—Zn—Cu (1%-1%-1%) on silica (60 Å) support at 400° C.

| Catalyst - Zr/Zn/Cu on silica (1%/1%/1%) | Day 1, Time = 60 min. | Day 1, Time = 180 min. | Day 1, Time Average | Day 2, Time = 60 min. | Day 2, Time = 120 min. | Day 2, Time 180 min. | Day 2, Time Average |
|---|---|---|---|---|---|---|---|
| Temperature, ° C. | 400 | 400 | 400 | 400 | 400 | 400 | 400 |
| LHSV, hr$^{-1}$ | 0.48 | 0.48 | 0.48 | 0.5 | 0.5 | 0.5 | 0.5 |
| Ethanlol:Acetaldehyde volumetric ratio | 4 | 4 | 4 | 4 | 4 | 4 | 4 |
| Ethanol conversion, wt. % | 31.52 | 21.35 | 26.43 | 25.27 | 26.56 | 26.77 | 26.20 |
| Acetaldehyde conversion, wt. % | 30.52 | 19.51 | 25.02 | 40.69 | −85.39 | −192.15 | −78.95 |
| Butadiene selectivity, mol. % | 17.56 | 26.29 | 21.93 | 30.36 | 78.65 | 25.96 | 44.99 |

TABLE 7-continued

Results of catalyst evaluation of ethanol:acetaldehyde over Zr—Zn—Cu (1%-1%-1%) on silica (60 Å) support at 400° C.

| Catalyst - Zr/Zn/Cu on silica (1%/1%/1%) | Day 1, Time = 60 min. | Day 1, Time = 180 min. | Day 1, Time Average | Day 2, Time = 60 min. | Day 2, Time = 120 min. | Day 2, Time 180 min. | Day 2, Time Average |
|---|---|---|---|---|---|---|---|
| Ethanol efficiency, mol. % | 23.01 | 34.12 | 28.56 | 46.03 | 45.10 | 13.66 | 34.93 |
| Acetaldehyde efficiency, mol. % | 80.68 | 124.57 | 102.62 | 96.97 | −114.91 | −31.33 | −16.42 |

As is evident from Tables 6 and 7, catalyst activity degraded over time. Without being bound by theory, the degradation of catalyst activity over time may be related to deactivation of the catalyst or coke formation, which may block pores of the catalyst. The trimetallic Zr/Zn/Cu (1 wt %/1 wt %/1 wt %) on silica (60 Å) required higher space velocities to approach similar butadiene yields observed for the bimetallic Zr/Zn (1.5 wt. %/0.5 wt. %) on silica (60 Å). Higher acetaldehyde production was observed for the trimetallic Zr/Zn/Cu (1 wt %/1 wt %/1 wt %) on silica (60 Å) than for the bimetallic Zr/Zn (1.5 wt. %/0.5 wt. %) on silica (60 Å). Without being bound by theory, the higher acetaldehyde production may contribute to the dehydrogenation of ethanol, and may allow a feed containing no acetaldehyde to be utilized in the presence of the trimetallic Zr/Zn/Cu (1 wt %/1 wt %/1 wt %) on silica (60 Å) for production of butadiene.

Example 9

Nb/Re supported on an Na-exchanged X-type Faujasite zeolite prepared in accordance with Example B was evaluated to determine if an increase in basicity of support may reduce direct dehydration of ethanol to ethylene and increase butadiene yield relative to the results observed with the Nb/Re supported on silica (Example 1). Experimental runs utilizing the experimental set-up shown in FIG. 4 were conducted using the Nb/Re supported on an Na-exchanged X-type Faujasite zeolite. The results at an LHSV 0.31 hr$^{-1}$ and a temperature of 325° C. yielded gaseous effluent with 48 mol. % 1,3-butadiene. The ethylene concentration was 19 mol. % of the gaseous effluent, indicating that direct dehydration of ethanol was occurring. At a temperature of 300° C., the gaseous effluent contained 7 mol. % ethylene and 34 mol. % butadiene. The amount of hydrogen present in the gaseous effluent was observed to increase over time, indicating dehydrogenation activity of the catalyst and insufficient aldol condensation to form crotonaldehyde to react further with ethanol. Ethylene was observed in the gaseous effluent, indicating catalytic activity for dehydration of ethanol. Table 8 shows the results for the various conditions tested in the experimental runs performed on the Nb/Re supported on an Na-exchanged X-type Faujasite zeolite.

TABLE 8

Comparative efficiencies using Nb/Re on Na—X zeolite

| Temperature, ° | 325 | 340 | 315 | 300 | 325 | 300 | 340 | 315 |
|---|---|---|---|---|---|---|---|---|
| LHSV, hr$^{-1}$ | 0.31 | 0.31 | 0.31 | 0.31 | 0.49 | 0.49 | 0.49 | 0.49 |
| Gaseous effluent flow rate, l/hr | 2.42 | 2.14 | 1.49 | 0.99 | 1.18 | 1.29 | 1.74 | 0.95 |
| Ethanol conversion, wt. % | 46.30 | 38.18 | 36.88 | 30.78 | 27.10 | 17.56 | 35.10 | 22.35 |
| Acetaldehyde conversion, wt. % | 59.32 | 50.22 | 54.80 | 54.49 | 32.12 | 30.09 | 36.04 | 37.55 |
| Butadiene process yield, mol. % | 4.45 | 5.42 | 3.00 | 2.65 | 3.65 | 2.86 | 3.06 | 2.44 |
| Butadiene selectivity, mol. % | 8.79 | 12.87 | 7.10 | 14.14 | 12.61 | 13.54 | 8.48 | 9.12 |
| Ethanol efficiency, mol. % | 12.60 | 18.60 | 10.67 | 11.30 | 17.66 | 31.39 | 11.43 | 14.31 |
| Acetaldehyde efficiency, mol. % | 31.60 | 45.44 | 23.08 | 20.51 | 47.88 | 40.10 | 35.76 | 27.37 |

Example 10

Experimental runs were performed utilizing the experimental set-up shown in FIG. 4, and using a 2% Ta supported on Na—X-zeolite prepared in accordance with Example C. A butadiene selectivity of 5.5 mol. % at a 30 wt. % conversion of ethanol was obtained using a temperature of 325° C. and an LHSV of 0.38 hr$^{-1}$. This result compared unfavorably to the results obtained utilizing the same reaction conditions, but with 2% Ta supported on a silica support as the catalyst system. Utilization of 2% Ta supported on a silica support as the catalyst system resulted in a 19 mol. % butadiene selectivity at a 26 wt. % conversion of ethanol. An experimental run performed utilizing the 2% Ta supported on Na—X-zeolite prepared in accordance with Example C, a temperature of 340° C., and an LHSV of 0.38 hr$^{-1}$ resulted in a butadiene selectivity of 4 mol. %.

Example 11

Experimental runs were performed on Zr (1.5 wt %)/Zn (0.5 wt %) catalyst supported on Na—X-zeolite. The butadiene selectivity observed at a temperature of 325° C. and an LHSV 0.4 hr$^{-1}$ was 2 mol. % at 20 wt. % ethanol conversion. Under the same reaction conditions, using a Zr (1.5 wt %)/Zn (0.5 wt %) catalyst supported on a silica support (DAVISIL® 646), a butadiene selectivity of 14 mol. % at a 22 wt. % ethanol conversion was observed.

Without being bound by theory, it is believed basicity of the catalyst influences the butadiene selectivity. It has been hypothesized that using a basic Na-exchanged zeolite as a support in place of a silica support would influence the butadiene selectivity. The direct dehydration of ethanol to ethylene is prevalent with the presence of acidic sites on the catalyst surface. The Na-exchange leaves behind some residual acidic sites. This residual acidity of the zeolite support may contribute to the observed increased selectivity to ethylene and carbon dioxide using Zr (1.5 wt %)/Zn (0.5 wt %) catalyst supported on Na—X-zeolite, leading to decreased butadiene selectivity. The results demonstrate that the use of basic zeolites as a support did not provide enhancement in butadiene yield in comparison to the use of silica as a support.

Example 12

MgO/$SiO_2$ supports were used to study the increased basicity of the support. Experimental runs were performed with an MgO (15 wt. %) promoted DAVISIL® 646 silica supported catalyst containing Zr (1.5 wt. %)/Zn (0.5 wt. %) utilizing the experimental set-up depicted in FIG. 4. The Zr (1.5 wt. %)/Zn (0.5 wt. %) supported on MgO (15 wt. %) promoted DAVISIL® 646 silica was prepared in accordance with Example E. At a temperature of 400° C., a butadiene selectivity of 17 mol. % at 25 wt. % a conversion of ethanol was observed, with a 9 mol. % overall butadiene yield. Experimental runs were performed with an MgO (15 wt. %) promoted DAVISIL® 636 silica (60 Å) supported catalyst with different dispersions and locations within the support. Without being bound by theory, magnesia is believed to activate the aldol condensation reaction and assist dehydrogenation of ethanol, while silica is believed to catalyze dehydration.

Figure 6:
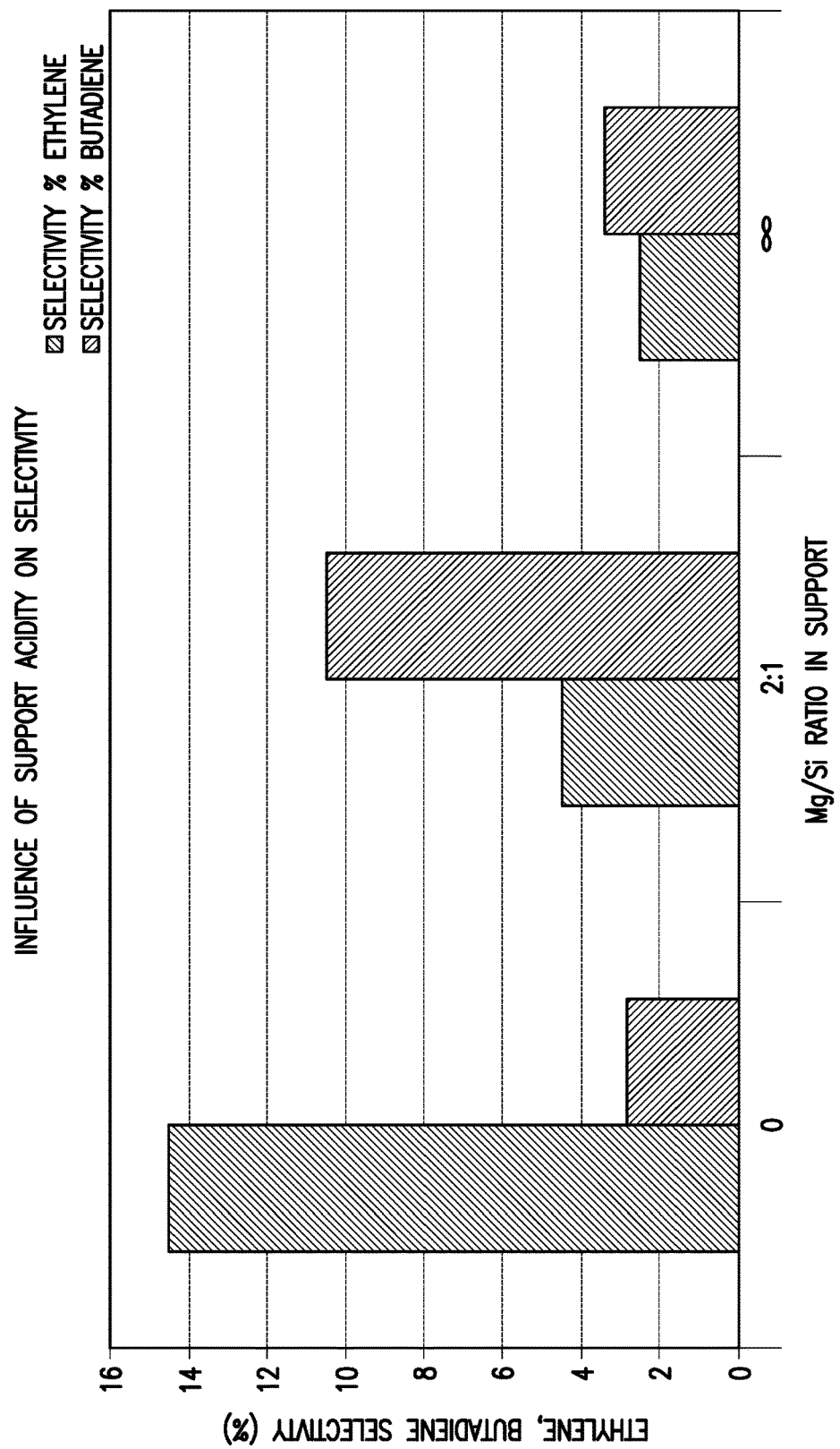
FIG. 6 is a bar graph depicting the influence of support acidity on butadiene and ethylene selectivity.

As seen in FIG. 6, the silica support exhibited greater selectivity to ethylene than to butadiene. The magnesia support exhibited lower ethylene selectivity than either the silica support or the magnesia-silica support. The magnesia-silica support had a Mg/Si molar ratio of 2:1, and exhibited increased butadiene selectivity compared with the magnesia support and the silica support.

Example 14

Experimental runs utilizing the experimental set-up shown in FIG. 4 were performed utilizing Nb—Re (2%-0.1%) supported on Na—X zeolite and Nb—Re (2%-0.1%) supported on K—X zeolite at a pressure of 50 psig. The Nb—Re (2%-0.1%) supported on Na—X zeolite and Nb—Re (2%-0.1%) supported on K—X zeolite were prepared in accordance with Example B. The results from the experimental runs are shown in Table 8.

TABLE 9

Results of catalyst evaluation at elevated pressures for ethanol to butadiene

| Catalyst | Pressure, psig | Temperature, ° C. | Ethanol:acetaldehyde volumetric ratio | LHSV, $hr^{-1}$ | Ethanol conversion, wt. % | Acetaldehyde conversion, wt. % | Butadiene selectivity, wt. % |
|---|---|---|---|---|---|---|---|
| 2% Nb—0.1% Re on Na X | 80 | 325 | 0.2:0.1 | 3.34 | 32.78 | 67.32 | 0.07 |
|  | 50 | 325 | 0.2:0.1 | 5.14 | 74.86 | 79.41 | 1.56 |
|  | 50 | 350 | 0.2:0.1 | 3.52 | 33.36 | 72.37 | 2.45 |
|  | 50 | 325 | 0.2:0.1 | 3.45 | 28.91 | 74.61 | 0.04 |
| 2% Nb—0.1% Re on K X | 50 | 325 | 0.2:0.1 | 1.54 | 23.97 | 86.57 | 0.28 |
|  | 50 | 300 | 0.2:0.1 | 1.58 | 17.63 | 82.99 | 0.17 |
|  | 50 | 300 | 0.9:0.1 | 1.59 | 9.20 | 63.17 | 0.02 | containing Zr (1.5 wt. %)/Zn (0.5 wt. %) prepared in accordance with Example E. Use of the MgO (15 wt. %) promoted DAVISIL® 636 silica (60 Å) supported catalyst containing Zr (1.5 wt. %)/Zn (0.5 wt. %) resulted in a butadiene selectivity of 19 mol. % at a 40 wt. % ethanol conversion and a temperature of 400° C., with a 9 mol. % overall butadiene yield.

Example 13

In order to elucidate the influence of basicity of the support on the conversion of ethanol to butadiene, experimental runs were conducted utilizing the experimental set-up shown in FIG. 4 to compare the catalytic activity of $SiO_2$, MgO, and MgO/$SiO_2$ supports. The ethylene selectivity (mol. %) and butadiene selectivity (mol. %) observed using undoped silica, magnesia-silica, and magnesia supports are shown in FIG. 6. Silica gel was used as the undoped silica. The formation of certain amounts of ethylene and acetaldehyde, as main byproducts, was observed on bare silica gel. Without being bound by theory, silica gel is not perfectly pure, consequently minor amounts of impurities or isolated silanols may introduce some acidity to silica gel. Thus, silica supports may be, at least to some extent, responsible for the formation of some intermediates during the conversion of ethanol to butadiene, as well as for the formation of ethylene, a major by-product of the ethanol to butadiene conversion.

The binary magnesia-silica support was prepared to contain both basic (magnesia) and acidic (silica) components The liquid effluent produced in the experimental runs of Example 14 contained a large number of components, some of which have been identified as low molecular weight oxygenates. The gaseous effluent contained methane, hydrogen, $CO_2$ and CO. Without being bound by theory, hydration of ethanol may yield methane and hydrogen.

The results indicate that no appreciable increase in yield of butadiene was obtained with the increased basicity of the catalyst supported on Na—X zeolite, as opposed to K—X zeolite.

Example 15

Experimental runs were conducted utilizing the experimental set-up depicted in FIG. 4 to observe the influence of recycling of the liquid effluent to the dehydration reactor as a co-feed, as shown in FIG. 1A. Modifications were made to the reactor system shown in FIG. 4 to allow the testing of the recycle concept shown in the process flow diagram in FIG. 1A by allowing the liquid effluent to be recycled back to the reactor inlet at a set flow rate. The feed and effluent compositions were analyzed to determine the conversion of ethanol and the selectivity of butadiene. The dehydration catalyst system used in this evaluation was a Zr/Zn/Cu (1%/1%/1%) supported on silica (60 Å) prepared in accordance with Example F.

Figure 7:
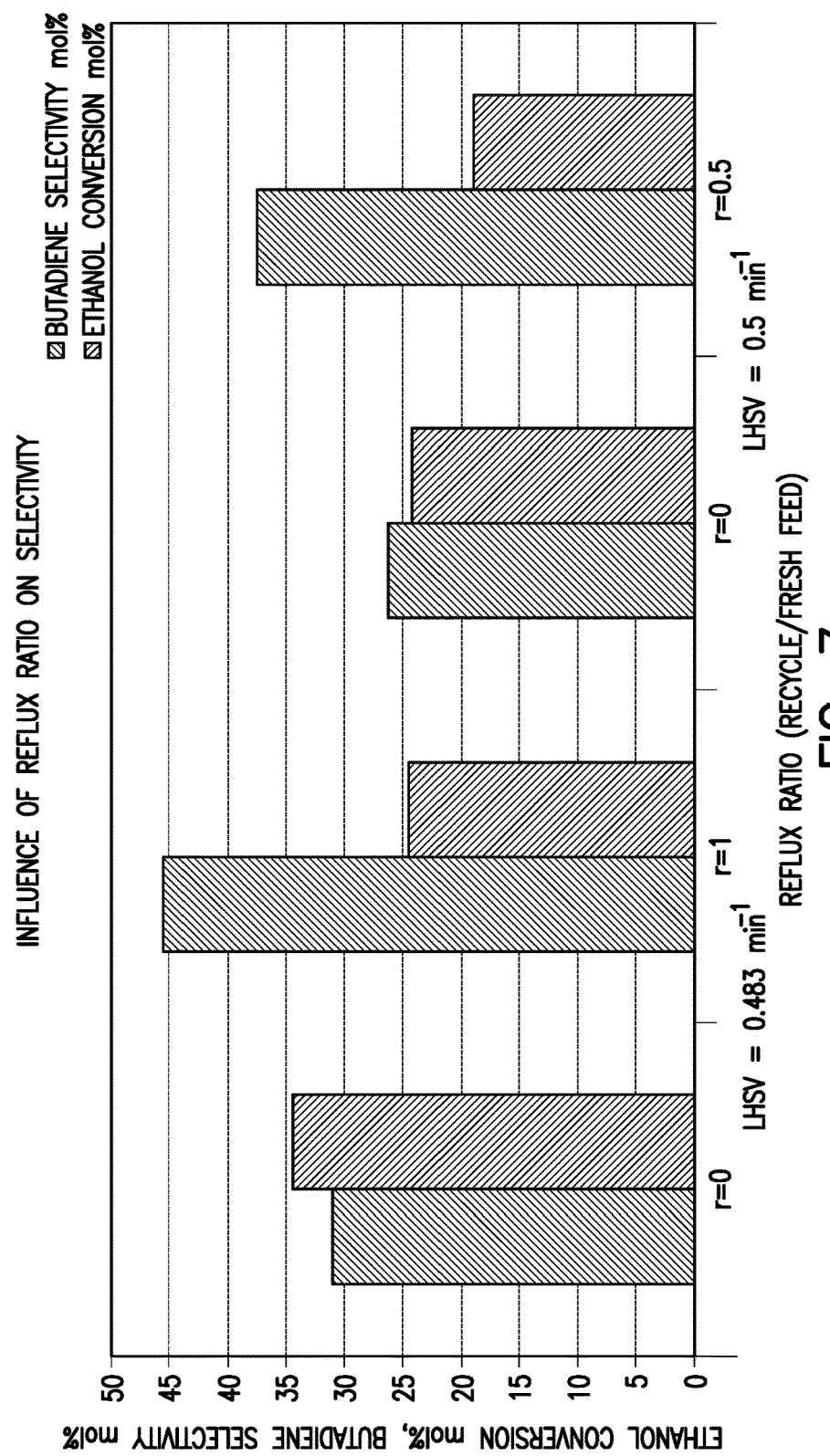
FIG. 7 is a bar graph depicting the influence of a recycle effluent and reflux ratio on butadiene selectivity.

The reflux ratio is the volumetric ratio of recycle effluent to fresh feed that was fed to the dehydration reactor. The reflux ratio was varied at different space velocities at a temperature of 400° C. The fresh feed, which had an ethanol to acetaldehyde volumetric ratio of 4:1, was maintained at the start of the experiment and, after establishing a baseline, the amount of fresh feed was reduced as the recycle effluent from the liquid separator was introduced to the static mixer along with the reduced fresh feed. The results, shown in FIG. 7, demonstrate that the butadiene selectivity was maintained or increased and the ethanol conversion was decreased with a reflux ratio of 0.5 and 1.0 (by volume).

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

What is claimed is:

1. A process comprising:
   reacting a feed stream comprising ethanol and aldehyde in a dehydration reactor in the presence of a dehydration catalyst system comprising a Group 4 metal oxide and a silica support wherein the dehydration catalyst system contains only a single metal oxide, wherein the single metal oxide is a Group 4 metal oxide;
   obtaining a product stream comprising butadiene from the dehydration reactor, wherein the process has a selectivity of butadiene of between 15 and 20 mole percent, a process yield of butadiene of 1 to 4 mole percent, an acetaldehyde efficiency of 10 to 50 mole percent, or an acetaldehyde conversion of from 35 to 75 percent; and
   regenerating the dehydration catalyst system in-situ in the presence of hydrogen at between 300 and 600° C.

2. The process of claim 1, wherein the Group 4 metal oxide is a zirconium metal oxide.

3. The process of claim 1, wherein the support comprises $MgO/SiO_2$.

4. The process of claim 1, further comprising, prior to reacting the feed stream comprising ethanol in the dehydration reactor, dehydrogenating a stream comprising ethanol in a dehydrogenation reactor using a catalyst comprising silver located upstream of the dehydration reactor to form the feed stream, wherein the feed stream comprises ethanol and acetaldehyde.

5. The process of claim 1, further comprising:
   obtaining a recycle stream containing unreacted ethanol from the dehydration reactor; and
   feeding the recycle stream into the dehydration reactor with the feed stream.

6. The process of claim 5, wherein the a reflux ratio ranges from 0.5 to 1.0, wherein the reflux ratio is a ratio of the amount of the recycle stream to the amount of the feed stream fed to the dehydration reactor, as determined by volume.

7. The process of claim 1, wherein the ethanol comprises bioethanol.

8. The process of claim 1, wherein a temperature in the dehydration reactor during reaction of the feed stream ranges from 148 to 500° C.

9. The process of claim 1, wherein a pressure in the dehydration reactor during reaction of the feed stream is from 0.01 to 0.6 MPa.

10. The process of claim 1, wherein a liquid hourly space velocity in the dehydration reactor during reaction of the feed stream is from 0.1 to 5 $hr^{-1}$.

11. The process of claim 1, wherein the feed stream comprises ethanol and acetaldehyde, and wherein a volumetric ratio of ethanol to acetaldehyde in the feed stream ranges from 9:1 to 1:1.

12. A process comprising:
    reacting a feed stream comprising ethanol in a dehydration reactor in the presence of a dehydration catalyst system wherein the dehydration catalyst system comprises a bimetallic catalyst system containing only two metal oxides, and wherein at least one of the two metal oxides is a Group 4 metal oxide;
    obtaining a product stream comprising butadiene from the dehydration reactor;
    obtaining a recycle stream containing unreacted ethanol, acetaldehyde, butadiene, diethyl ether, or combinations thereof from the dehydration reactor;
    feeding the recycle stream into the dehydration reactor with the feed stream; and
    regenerating the dehydration catalyst system in-situ in the presence of hydrogen at between 300 and 600° C.

13. The process of claim 12, wherein the dehydration catalyst system comprises a cobalt-zirconium oxide, or a cerium-zirconium oxide.

14. The process of claim 12, wherein the dehydration catalyst system comprises Zr/Zn oxides supported on silica or Zr/Zn oxides supported on magnesia silica.

15. A process comprising:
    reacting a feed stream comprising ethanol in a dehydration reactor in the presence of a dehydration catalyst system wherein the dehydration catalyst system comprises a trimetallic catalyst system containing only three metal oxides, and wherein at least one of the three metal oxides is a Group 4 metal oxide;
    obtaining a product stream comprising butadiene from the dehydration reactor;
    obtaining a recycle stream containing unreacted ethanol from the dehydration reactor;
    feeding the recycle stream into the dehydration reactor with the feed stream; and
    regenerating the dehydration catalyst system in-situ in the presence of hydrogen at between 300 and 600° C.

16. The process of claim 7, wherein the dehydration catalyst system comprises Zr/Zn/Cu oxides supported on silica, or Zr/Zn/Cu oxides supported on magnesia-silica.

* * * * *